(12) United States Patent
Holloway et al.

(10) Patent No.: US 6,245,529 B1
(45) Date of Patent: Jun. 12, 2001

(54) TESTIS-SPECIFIC CYSTATIN-LIKE PROTEIN CYSTATIN T

(75) Inventors: James L. Holloway, Seattle; Andrew L. Feldhaus, Lynnwood, both of WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/617,302

(22) Filed: Jul. 17, 2000

Related U.S. Application Data

(63) Continuation-in-part of application No. 09/431,480, filed on Nov. 1, 1999
(60) Provisional application No. 60/156,382, filed on Sep. 28, 1999, and provisional application No. 60/109,217, filed on Nov. 20, 1998.

(51) Int. Cl.[7] .................................................. C12N 15/09
(52) U.S. Cl. .................................. 435/69.2; 435/252.33; 435/320.1; 435/69.1; 536/23.4; 536/23.5; 530/350
(58) Field of Search ............................. 435/69.2, 252.33, 435/320.1, 69.1; 536/23.4, 23.5; 530/350

(56) References Cited

U.S. PATENT DOCUMENTS 6,011,012 * 1/2000 Ni et al. .................................. 514/12

OTHER PUBLICATIONS

Murine EST OST 13804, Lexicon Genetics, 1998.
Soares, Program for Rat Gene Discovery and Mapping, 1998. Genbank Accession Number Al 030491.
Cornwall, *Mol. Endo.* 6: 1653–64, 1992. Accession Number S49926.
Cornwall et al, *Mol. Endocrin.* 6: 1653–64, 1992.
Bobek et al., *Biochem. J.* 278: 627–635, 1991.
Ni et al., *J. Biol. Chem.* 273: 24797–24804, 1998.
Ni et al., *J. Biol. Chem.* 272: 10853–10858, 1997.
Abrahamson et al., *FEBS LETT.* 216 229–233, 1987.
Sotiropoulou et al., *J. Biol. Chem.* 272: 903–910, 1997.
Esnard et al., *FEBS LETT.* 300: 131–135, 1992.
Tsuruta et al., *Biol. Of Reproduction* 49: 1045–1054, 1993.
Peloille et al., *Eur. J. Biochem.* 244: 140–146, 1997.
Mruk et al., *J. Androl.* 18: 612–622, 1997.
Tohonen et al., *Proc. Natl. Acad. Sci. USA* 95: 14208–14213, 1998.
Freije et al., *J. Biol. Chem.* 266: 20538–20543, 1991.
Turk & Bode, *FEBS LETT.* 285: 213–219, 1991.

* cited by examiner

*Primary Examiner*—Nashaat T. Nashed
*Assistant Examiner*—Christian L. Fronda
(74) *Attorney, Agent, or Firm*—Susan Lingenfelter

(57) ABSTRACT

The present invention relates to cystatin T (also known as zcys3) polypeptides and polynucleotides encoding the same. Cystatin T polypeptide is testis specific and homologous to cystatin-related epididymal specific gene (CRES) and type 2 cystatins. The polypeptides would be useful for modulating spermatogenesis and may be used to study or modulate that function in in vitro or in vivo systems. The present invention also includes antibodies to the cystatin T polypeptides.

14 Claims, No Drawings

TESTIS-SPECIFIC CYSTATIN-LIKE PROTEIN CYSTATIN T

REFERENCE TO RELATED APPLICATIONS

This application is a continuation in part of U.S. patent application Ser. No. 09/431,480, filed on Nov. 1, 1999, which is related to Provisional Applications 60/109,217, filed on Nov. 20, 1998 and 60/156,382 filed on Sep. 28, 1999. Under 35 U.S.C. §119(e) (1), this application claims benefit of said Provisional Applications.

BACKGROUND OF THE INVENTION

The cystatin superfamily is an evolutionarily related group of proteins consisting of at least three families, i.e., stefins (type 1), cystatins (type 2), and kininogens (type 3). See, for example, Barrett, *TIBS* 12: 193–196, 1987. Generally, stefin family members are unglycosylated proteins consisting of about 100 amino acids that are devoid of disulfide bonds. In contrast, cystatin family members are proteins consisting of about 115 amino acids and characterized by two disulfide bonds in the carboxy-terminal region of the protein. Finally, kininogens contain three regions containing two disulfide loops, similar to the carboxy terminal domain found in members of the cystatin family. The cystatin superfamily are inhibitors of cysteine proteinases (also referred to as cysteine proteases) and are believed to function in a protective role with regard to pathological action of endogenous or exogenous cysteine proteinases. It is believe that cystatins form equimolar reversible complexes with cysteine proteinases.

Cystatin-like proteins have also been identified. One such protein, cystatin-related epididymal specific gene (CRES) does not contain the conserved sequence motifs necessary for cysteine proteinase inhibitory activity (Cornwell et al., *Mol. Endocrinol.* 6:1653–64, 1992 and Cornwell and Hann, *Mol. Reprod. Dev.* 41:37–46, 1995). Also, unlike the ubiquitous expression of many of the cystatins, CRES is restricted to the proximal caput epididymal epithelium and testis. CRES expression is stage specific during spermatogenesis and CRES is found in both round and elongating spermatids suggesting a specialized role during spermatogenesis. Cystatins are also found with male reproductive tissues and secretions. Cystatin C for example is found in highest abundance in human semen and participates in spermatogenesis and spermiogenesis and is associated with the sperm throughout its time in the male genital tract (Esnard wt al., *FEBS Lett.* 300:131–5, 1992). Testatin is believed to be involved in early testis development. Expression is restricted to fetal gonads and adult testis and it is expressed during testis cord formation in pre-Sertoli cells (T öhönen et al., *Proc. Natl. Acad. Sci. USA* 95:14208–13, 1998).

Proteins capable of modulating spermatogenesis are sought for the study, diagnosis and treatment of conditions associated with reproductive disorders. The present invention provides such polypeptides for these and other uses that should be apparent to those skilled in the art from the teachings herein.

SUMMARY OF THE INVENTION

Within one aspect the invention provides an isolated polypeptide comprising 10 or more contiguous amino acid residues of SEQ ID NO:2, wherein the polypeptide comprises SEQ ID NO:14 and specifically binds to an antibody to which a polypeptide of SEQ ID NO:2 specifically binds. Within one embodiment the polypeptide comprises SEQ ID NO:13. Within another embodiment the polypeptide comprises amino acid residues 76–138 of SEQ ID NO:2. Within yet another embodiment the polypeptide further comprises an affinity tag or binding domain.

The invention also provides an isolated polypeptide comprising a sequence of amino acid residues that is selected from the group consisting of: a) a sequence of amino acid residues that is 80% identical to the amino acid sequence of SEQ ID NO:2, wherein the sequence comprises cysteine residues corresponding to amino acid residues 94, 104, 118 and 138 of SEQ ID NO:2 and wherein the polypeptide comprising the amino acid sequence specifically binds with an antibody that specifically binds with a polypeptide having the amino acid sequence of SEQ ID NO:2; and b) a sequence of amino acid residues encoded by a polynucleotide sequence which hybridizes under stringent conditions to a similarly sized polynucleotide sequence of SEQ ID NO:1. Within one embodiment any difference between the amino acid sequence of the isolated polypeptide and the corresponding amino acid sequence of SEQ ID NO:2 is due to a conservative amino acid substitution. Within another embodiment amino acid percent identity is determined using a FASTA program with ktup=1, gap opening penalty=10, gap extension penalty=1, and substitution matrix=blosum62, with other parameters set as default.

The invention also provides an isolated polypeptide consisting of amino acid residues 76–138 of SEQ ID NO:2. Additionally the invention provides an isolated polypeptide comprising the amino acid sequence of SEQ ID NO:2.

Within another aspect of the invention is provided a fusion protein comprising a secretory signal sequence having the amino acid sequence of amino acid residues 1–20 of SEQ ID NO:2, wherein the secretory signal sequence is operably linked to an additional polypeptide. In one embodiment the first portion comprising a polypeptide as described above; and the second portion comprising another polypeptide.

Within yet another aspect of the invention is provided an isolated polynucleotide encoding a polypeptide as described above. Within one embodiment the polypeptide comprises SEQ ID NO:13. Within another embodiment the polypeptide comprises amino acid residues 76–138 of SEQ ID NO:2. Within another embodiment the polynucleotide encodes a polypeptide further comprising an affinity tag or binding domain.

The invention also provides an isolated polynucleotide molecule that encodes a polypeptide, wherein the polypeptide comprises a sequence of amino acid residues that is selected from the group consisting of: a) a sequence of amino acid residues that is 80% identical to the amino acid sequence of SEQ ID NO:2, wherein the sequence comprises cysteine residues corresponding to amino acid residues 94, 104, 118 and 138 of SEQ ID NO:2 and wherein the polypeptide comprising the amino acid sequence specifically binds with an antibody that specifically binds with a polypeptide having the amino acid sequence of SEQ ID NO:2; b) degenerate nucleotide sequence of a); c) nucleotide sequences complementary to a) or b); and d) a sequence of amino acid residues encoded by a polynucleotide sequence which hybridizes under stringent conditions to a similarly sized polynucleotide sequence of SEQ ID NO:1. Within one embodiment any difference between the amino acid sequence encoded by the polynucleotide molecule and the corresponding amino acid sequence of SEQ ID NO:2 is due to one or more conservative amino acid substitutions. Within another embodiment the amino acid percent identity is determined using a FASTA program with ktup=1, gap opening penalty=10, gap extension penalty=1, and substitution matrix=blosum62, with other parameters set as default.

The invention also provides an isolated polynucleotide molecule consisting of nucleotides 271–459 of SEQ ID NO:1. The invention further provides an isolated polynucleotide molecule comprising the nucleotide sequence of nucleotides 46 to 468 of SEQ ID NO:1.

The invention provides a polynucleotide encoding a fusion protein comprising a secretory signal sequence having the amino acid sequence of amino acid residues 1–20 of SEQ ID NO:2, wherein the secretory signal sequence is operably linked to an additional polypeptide. Within one embodiment the first portion comprises a polypeptide as described above; and the second portion comprising another polypeptide.

Within another aspect the invention provides an expression vector comprising the following operably linked elements: a transcription promoter; a DNA segment encoding a polypeptide as described above; and a transcription terminator. Within one embodiment the expression vector further comprises a secretory signal sequence operably linked to the polypeptide encoded by the DNA segment. Within another aspect the DNA segment encodes a polypeptide covalently linked amino terminally or carboxy terminally to an affinity tag. Within yet another embodiment is provided a cultured cell into which has been introduced an expression vector as described above, wherein the cultured cell expresses the polypeptide encoded by the DNA segment. Another embodiment provides a method of producing a polypeptide comprising: culturing a cell into which has been introduced an expression vector as described above; whereby the cell expresses the polypeptide encoded by the DNA segment; and recovering the expressed polypeptide.

Within another aspect the invention provides an antibody or antibody fragment that specifically binds to a polypeptide as described above. Within one embodiment the antibody is selected from the group consisting of: a) polyclonal antibody; b) murine monoclonal antibody; c) humanized antibody derived from b); and d) human monoclonal antibody. Within another embodiment the antibody fragment is selected from the group consisting of F(ab'), F(ab), Fab', Fab, Fv, scFv, and minimal recognition unit. Within yet another embodiment is provided an anti-idiotype antibody that specifically binds to the antibody as described above.

Within yet another aspect the invention provides a polypeptide as described above, in combination with a pharmaceutically acceptable vehicle.

These and other aspects of the invention will become evident upon reference to the following detailed description. In addition, various references are identified below and are incorporated by reference in their entirety.

DETAILED DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952–4, 1985), substance P, Flag™ peptide (Hopp et al., *Biotechnology* 6:1204–10, 1988), streptavidin binding peptide, or other antigenic epitope or binding domain. See, in general, Ford et al., *Protein Expression and Purification* 2: 95–107, 1991. DNAs encoding affinity tags are available from commercial suppliers (e.g., Pharmacia Biotech, Piscataway, N.J.).

The term "variant" denotes any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides and proteins. Where the context allows, these terms are used with reference to a particular sequence or portion of a polypeptide or protein to denote proximity or relative position. For example, a certain sequence positioned carboxyl-terminal to a reference sequence within a polypeptide or protein is located proximal to the carboxyl terminus of the reference sequence, but is not necessarily at the carboxyl terminus of the complete polypeptide or protein.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985). When applied to a polypeptide or protein, the term "isolated" indicates that the polypeptide or protein is found in a condition other than its native environment, such as apart from blood and animal tissue. In a preferred form, the isolated polypeptide or protein is substantially free of other proteins, particularly other proteins of animal origin. It is preferred to provide the protein in a highly purified form, i.e., greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, denotes that the segments are arranged so that they function in concert for their intended purposes, e.g. transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, a-globin, b-globin, and myo-globin are paralogs of each other.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

"Probes and/or primers" as used herein can be RNA or DNA. DNA can be either cDNA or genomic DNA. Polynucleotide probes and primers are single or double-stranded DNA or RNA, generally synthetic oligonucleotides, but may be generated from cloned cDNA or genomic sequences or its complements. Analytical probes will generally be at least 20 nucleotides in length, although somewhat shorter probes (14–17 nucleotides) can be used. PCR primers are at least 5 nucleotides in length, preferably 15 or more nt, more preferably 20–30 nt. Short polynucleotides can be used when a small region of the gene is targeted for analysis. For gross analysis of genes, a polynucleotide probe may comprise an entire exon or more. Probes can be labeled to provide a detectable signal, such as with an enzyme, biotin, a radionuclide, fluorophore, chemiluminescer, paramagnetic particle and the like, which are commercially available from many sources, such as Molecular Probes, Inc., Eugene, Oreg., and Amersham Corp., Arlington Heights, Ill., using techniques that are well known in the art.

The term "promoter" denotes a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-domain structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. Most nuclear receptors also exhibit a multi-domain structure, including an amino-terminal, transactivating domain, a DNA binding domain and a ligand binding domain. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery of a novel DNA sequence that encodes a cystatin T (also known as zcys3), polypeptide having homology to the cystatin family of proteins (i.e., cystatin superfamily type 2 proteins). Indicia of such homology are the four cysteine residues in the carboxy terminal portion of the protein (at positions 94, 104, 118 and 138 of SEQ ID NO: 2), which are believed to form two disulfide bonds thereby generating the characteristic two disulfide loop structure of the cystatin family.

Novel cystatin T polypeptides of the present invention were initially identified by selecting ESTs from an EST database and predicting the protein sequences thereof. Selected EST/corresponding protein sequences were associated with the most similar functionally characterized polynucleotide or polypeptide sequence using indexing software. ESTs homologous to secreted proteins having interesting associated biological activities were selected for further study. A single EST sequence was discovered and predicted to be a mouse paralogue of the murine cystatin-related epididymal specific protein precursor CRES (SEQ ID NO:3), murine Testatin (SEQ ID NO:18), human cystatin C precursor (SEQ ID NO:6), cystatin D precursor (SEQ ID NO:7) and cystatin SN precursor (CYTN_HUMAN) known cysteine proteinase inhibitors of the cystatin family (i.e., cystatin superfamily type 2). See, for example, Abrahamson et al., FEBS Lett. 216 229–33, 1987.

When compared with other members of the cystatin family, especially human and mouse CRES, the cystatin T polypeptides were found to contain a motif QX(6)YX(10)CXKX(7–12)CX(13)CX(7)PWX(10)C (SEQ ID NO:13) located at amino acid residues 76–138 of SEQ ID NO:2, wherein X( ) represents the number of amino acid residues between the identified amino acid residues. X represents any amino acid residue, Q represents glutamine, Y represents tyrosine, C represents cysteine, K represents lysine, P represents proline and W represents tryptophan. Within this motif is a cysteine motif that appears to be unique to cystatin superfamily proteins. The cysteine motif is represented by the formula CX{8, 9 or 10}CX{13}CX{19}C, (SEQ ID NO:14) wherein X{ } is the number of amino acid residues between cysteines (C). This motif can be found at amino acid residues 94–138 of SEQ ID NO:2. This cysteine motif appears to occur in all known members of the cystatin family (for example, human cystatins C, S, T, N, D, bovine cystatin, chick cystatin, rat cystatins C and S, mouse cystatin C, Testatin and the like).

X-ray analysis of chicken egg white cystatin (Bode et al., EMBO J. 7, 2593–99, 1988) and directed mutagenesis studies (Auerswald et al., Eur. J. Biochem. 209:837–45, 1992) revealed three regions to be important for cysteine proteinase inhibitory activity, the Gly9 residue, the Gln53, Val55, Gly57 motif, and the carboxy terminal Pro103, Trp104 motif. Only the Pro103, Trp104 motif and the Gln53 residue are conserved in CRES while Testatin retains only the Val55 and Pro103, Trp104 motif. It is not clear if the substrate specificity of these members is altered or if these proteins lack the ability to ihibit cysteine proteinases. Töhonen et al. Proc. Natl. Acad. Sci. USA 95:14208–13, 1998, propose that these two genes comprise a subgroup within the family 2 cysteins. Cystatin T also contains a subset of these motif, having the only the Gln53 (amino acid residue 76 of SEQ ID NO:2) residue of the Gln53, Val55, Gly57 region although within this region (amino acid residues 76–79 of SEQ ID NO:2) the four residues are identical to those present in CRES. Cystatin T also contains the Pro103, Trp104 (amino acid residues 126–137 of SEQ ID NO:2) and a Gly residue near the amino terminus (amino acid residue 76 of SEQ ID NO:2) but the spacing is not consistent with that observed for other family members. These similarities between cystatin T, CRES and Testatin suggest they form a new family 2 subclass.

Cystatin T links to murine chromosome 2 framework marker d2mit194 located at 81.4 cm. The human locus for this position is 20p11.2, which contains the cystatin gene cluster (five cystatin genes, CST1 to 5, and two pseudogenes, Thiesse et al., DNA Cell Biol. 13:97–116, 1994) that spans less than 905 kb. Members of family 1 and 3 have been mapped to the long arm of chromosome 3 (Tsui et al., Genomics 15:507–14, 1993, and James et al., Genomics 32:425–30, 1996) further suggesting that cystatin T is a member of the family 2 cystatins.

Analysis of the tissue distribution of the mRNA corresponding to this novel DNA by both Northern blot and Dot blot showed selective expression in murine testis. One transcript size was observed at approximately 1.0 Kb. The polypeptide encoded by that polynucleotide sequence has been designated cystatin T. Human tissue Northern blots probed with murine sequence indicated expression of a 1.0 Kb transcript in trachea. Cystatin T expression is quite distinct from other family 2 cystatins with the exception of CRES and Testatin. CRES is found primarily in the proximal caput region of the epididymis in addition to low expression in testis (Cornwell et al., Mol. Endo. 6:1653–64, 1992). Testatin expression is restricted to pre-Sertoli cells in fetal tissue and to Sertioli cells in adult testis (Töhönen et al., ibid.). Cystatin T mRNA expression is high in primary testis, it was not detected in the testis cell lines tested which may suggest that like CRES (Cornwell et al., ibid.) it is dependent on a various hormones in the testis, or is not expressed in these cell lines.

Analysis of the DNA encoding a cystatin T polypeptide (SEQ ID NO:1) revealed an open reading frame encoding 141 amino acids (SEQ ID NO: 2) comprising a signal peptide of 20 amino acid residues (residues 1–20 of SEQ ID NO: 2, nucleotides 57–105 of SEQ ID NO:1) and a mature polypeptide of 121 amino acids (residues 21–141 of SEQ ID NO: 2, nucleotides 106–468 of SEQ ID NO:1). Those skilled in the art will recognize that predicted secretory signal sequence domain boundaries are approximations based on primary sequence content, and may vary slightly; however, such estimates are generally accurate to within ±4 amino acid residues.

It is generally believed that under selective pressure for organisms to acquire new biological functions new cystatin superfamily members arose from duplication of existing receptor genes leading to the existence of multi-gene families. Family members thus contain vestiges of the ancestral gene, and these characteristic features can be exploited in the isolation and identification of additional family members. The cystatin superfamily is subdivided into stefins, cystatins and kininogens. Stefins are single chain proteins of $M_r$ of about 11,000 that lack disulfide bonds and carbohydrates. Cystatins are single chain proteins characterized by the presence of two disulfide bonds in the carboxy terminal region thereof. Moreover, cystatins are composed of about 115 amino acids with $M_r$ of about 13,000. Some cystatins exhibit phosphorylated and dephosphorylated forms. Kininogens are higher molecular weight moieties that contain three regions of homology to cystatins (i.e., three sets of two disulfide loops); however, only two of such regions are believed to be active. See, for example, Turk and Bode, FEBS Lett. 285(2): 213–9, 1991; Barrett, TIBS 12: 193–6, 1987; and Bobek and Levine, Crit. Rev. Oral Biol. Med. 3: 307–32, 1992.

Cystatin T shares 37.1% identity at the amino acid level with both murine (SEQ ID NO:3) and human (SEQ ID NO:4) CRES (Cornwall et al., Mol. Endocrinol. 6:1653–64, 1992). Cystatin T is slightly less identical to other members of the cystatin family. At the amino acid level, Cystatin T shares 28.3% identity with cystatin C_mouse (Solem et al., *Biochem. Biophys. Res. Comm.* 172:945–51, 1990, SEQ ID NO:5); 30.0% identity with cystatin C_HUMAN (Abrahamson et al., *FEBS Lett.* 216(2): 229–33, 1987, SEQ ID NO:6); 27.2% identity with cystatin D_HUMAN (Freije et al., *J. Biol. Chem.* 266(30): 20538–43, 1991, SEQ ID NO:7); 24.0% identity with cystatin E_HUMAN (Ni et al., *J. Biol. Chem.* 272:10853–8, 1997, SEQ ID NO:8); 23.8% identity with cystatin F_HUMAN (Ni et al., *J. Biol. Chem.* 273:24797–804, 1998, SEQ ID NO:9); 25.3% identity with cystatin M_HUMAN (Sotiropoulou et al., *J. Biol. Chem.* 373:903–10, 1997, SEQ ID NO:10); 26.9% identity with cystatin S_HUMAN (Bobek et al., *Biochem. J.* 278: 627–35, 1991, SEQ ID NO:11), 28.3% identity with cystatin SA-I_HUMAN (Al-Hashim et al., *J. Biol. Chem.* 263:9381–87, 1988, SEQ ID NO:12) and 18.8% identity with Testatin (Töhönen et al., *Proc. Natl. Acad. Sci. USA.*95:14208–13, 1998).

Regulation of reproductive function in males and females is controlled in part by feedback inhibition of the hypothalamus and anterior pituitary by blood-bone hormones. Testis proteins, such as activins and inhibins, have been shown to regulate secretion of active molecules including follicle stimulating hormone (FSH) for the pituitary (Ying, *Endocr. Rev.* 9:267–93, 1988; Plant et al., *Hum. Reprod.* 8:41–44, 1993). CRES gene expression is thought to be regulated by testicular factors or hormones (Cornwall et al., *Mol. Endo.* 6:1653–64, 1992). These functions may also be associated with the cystatin T proteins and may be used to regulate testicular functions.

Spermatogenesis is the sequential process whereby germ cells ultimately mature into spermatozoa, herein referred to as sperm. Testis-specific factors that influence the maturation process may come directly from the Sertoli cells that are in contact with spermatogenic cells, or may be paracrine or endocrine factors. Many of the molecules produced outside the seminiferous tubules are transported into the sperm cell microenvironment by transport and binding proteins that are expressed by the Sertoli cells within the seminiferous tubules.

Paracrine factors that cross the cellular barrier and enter the sperm cell microenvironment include molecules secreted from cells Leydig cells. Leydig cells are located in the interstitial space found between the seminiferous tubules in the testis, and produce several factors believed to play an important role in spermatogenic cell maturation process, such as testosterone, Leydig factor, IGF-1, inhibin and activin. The expression of these, and other factors, may be specific to a defined stage in the spermatogenic cycle. Cystatin T expression was not detected in epididymus or seminal vesicles suggesting that it might be expressed by interstitial cells.

Molecules acting in the early stages of spermatogenesis may be involved in such activities as sperm proliferation and development. Such molecules could act to enhance sperm development. CRES expression is stage-specific during spermatogenesis and is exclusively expressed by round spermatids at Stages VII–VIII and by early elongating spermatids of Stages IX and X (Cornwall and Hann, *Mol. Reprod. Dev.* 41:37–46, 1995).

Those molecules acting at a later stage in spermatogenesis may be involved in sperm motility and egg-sperm interactions. Such molecules could also act to enhance the activity of cryopreserved sperm. Assays evaluating such activities are known (Rosenberger, *J. Androl.* 11:89–96, 1990; Fuchs, *Zentralbl Gynakol* 11:117–20, 1993; Neurwinger et al., *Andrologia* 22:335–9, 1990; Harris et al., *Hum. Reprod.* 3:856–60, 1988; and Jockenhovel, *Andrologia* 22:171–8, 1990; Lessing et al., *Fertil. Steril.* 44:406–9 (1985); Zaneveld, In Male Infertility Chapter 11, Comhaire Ed., Chapman & Hall, London 1996).

Proteolysis-regulated testis-specific functions, including regulation of interactions between various cell types in the seminiferous tubule during spermatogenesis as well as migration of germ cells and release of spermatids (Monsees et al., *Adv. Exp. Med. Biol.* 424:111–23, 1997), suggest a role for the cystatins in the male reproduction process. Cysteine proteinases, such as cathepsin L, are present in latent form in the spermatozoa. Inhibitors of cysteine proteinases, such as cystatin C which is found in abundance in testis, epididymis, prostate and seminal vesicles may play a role in controlling proteolytic activity. Cystatin-like proteins such as cystatin T which have alterations in sequences thought to be necessary for inhibition of known proteinases may serve to inhibit as yet unidentified proteinases and could also serve to modulate proteinase activity in the testis. Cystatin T may regulate testis-specific cysteine proteinases such as testis-thymus expressed cathepsin V (Brömme et al., *Biochem.* 38:2377–85, 1999). Molecules having such activities are expected to result in enhanced fertility and successful reproduction. Antagonists of such molecules would be useful in contraceptive applications.

Proteins of the present invention would find application in enhancing fertilization during assisted reproduction in humans and in animals. Such assisted reproduction methods are known in the art and include artificial insemination, in vitro fertilization, embryo transfer and gamete intrafallopian transfer. Such methods are useful for assisting men and women who may have physiological or metabolic disorders that prevent natural conception. Such methods are also useful in animal breeding programs, such as for livestock, zoological, endangered species or racehorse breeding, and could be used within methods for the creation of transgenic animals.

Proteins of the present invention can be used to enhance sperm production, to increase the number of viable sperm in a sample, or be combined with sperm, an egg or an egg-sperm mixture prior to fertilization of the egg to enhance fertilization. The washed sperm or sperm removed from the seminal plasma used in such assisted reproduction methods has been shown to have altered reproductive functions, in particular, reduced motility and zona interaction. To enhance fertilization during assisted reproduction methods sperm is capacitated using exogenously added compounds. Suspension of the sperm in seminal plasma from normal subjects or in a "capacitation media" containing a cocktail of compounds known to activate sperm, such as caffeine, dibutyl cyclic adenosine monophosphate (dbcAMP) or theophylline, have resulted in improved reproductive function of the sperm, in particular, sperm motility and zonae penetration (Park et al., *Am. J. Obstet. Gynecol.* 158:974–9, 1988; Vandevoort et al., Mol. Repro. Develop. 37:299–304, 1993; Vandevoort and Overstreet, *J. Androl.* 16:327–33, 1995). Polypeptides of the present invention can used in such methods to enhance viability of cryopreserved sperm, enhance sperm motility and enhance fertilization, particularly in association with methods of assisted reproduction.

In cases where pregnancy is not desired, cystatin T proteins or protein fragments may function as germ-cell-specific antigens for use as components in "immunocontraceptive" or "anti-fertility" vaccines to induce formation of antibodies and/or cell mediated immunity to selectively inhibit a process, or processes, critical to successful reproduction in humans and animals. The use of sperm and testis antigens in the development of an immunocontraceptive have been described (O'Hern et al., *Biol Reprod.* 52:311–39, 1995; Diekman and Herr, *Am. J. Reprod. Immunol.* 37:111–17, 1997; Zhu and Naz, *Proc. Natl. Acad. Sci. USA* 94:4704–9,1997). A vaccine based on human chorionic gonadotrophin (HCG) linked to a diphtheria or tetanus carrier is currently in clinical trials (Talwar et al., *Proc. Natl. Acad. Sci. USA* 91:8532–36, 1994). A single injection resulted in production of high titer antibodies that persisted for nearly a year in rabbits (Stevens, *Am. J. Reprod. Immunol.* 29:176–88, 1993). Such methods of immunocontraception using vaccines would include testis specific proteins such as cystatin T or fragment thereof. The cystatin T protein or fragments can be conjugated to a carrier protein or peptide, such as tetanus or diphtheria toxoid. An adjuvant, as described above, can be included and the protein or fragment can be noncovalently associated with other molecules to enhance intrinsic immunoreactivity. Methods for administration and methods for determining the number of administrations are known in the art. Such a method might include a number of primary injections over several weeks followed by booster injections as needed to maintain a suitable antibody titer.

The present invention also provides polynucleotide molecules, including DNA and RNA molecules, that encode the cystatin T polypeptides disclosed herein. Those skilled in the art will readily recognize that, in view of the degeneracy of the genetic code, considerable sequence variation is possible among these polynucleotide molecules. SEQ ID NO:15 is a degenerate DNA sequence that encompasses all DNAs that encode the cystatin T polypeptide of SEQ ID NO:2. Those skilled in the art will recognize that the degenerate sequence of SEQ ID NO:15 also provides all RNA sequences encoding SEQ ID NO:2 by substituting U (uracil) for T (thymine). Thus, cystatin T polypeptide-encoding polynucleotides comprising nucleotide 1 to nucleotide 423 of SEQ ID NO:15 and their RNA equivalents are contemplated by the present invention. Table 1 sets forth the one-letter codes used within SEQ ID NO:15 to denote degenerate nucleotide positions. "Resolutions" are the nucleotides denoted by a code letter. "Complement" indicates the code for the complementary nucleotide(s). For example, the code Y denotes either C (cytosine) or T, and its complement R denotes A (adenine) or G (guanine), A being complementary to T, and G being complementary to C.

TABLE 1

| Nucleotide | Resolution | Nucleotide | Complement |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:15, encompassing all possible codons for a given amino acid, are set forth in Table 2.

TABLE 2

| Amino Acid | One Letter Code | Codons | | | | | | Degenerate Codon |
|---|---|---|---|---|---|---|---|---|
| Cys | C | TGC | TGT | | | | | TGY |
| Ser | S | AGC | AGT | TCA | TCC | TCG | TCT | WSN |
| Thr | T | ACA | ACC | ACG | ACT | | | ACN |
| Pro | P | CCA | CCC | CCG | CCT | | | CCN |
| Ala | A | GCA | GCC | GCG | GCT | | | GCN |
| Gly | G | GGA | GGC | GGG | GGT | | | GGN |
| Asn | N | AAC | AAT | | | | | AAY |
| Asp | D | GAC | GAT | | | | | GAY |
| Glu | E | GAA | GAG | | | | | GAR |
| Gln | Q | CAA | CAG | | | | | CAR |
| His | H | CAC | CAT | | | | | CAY |
| Arg | R | AGA | AGG | CGA | CGC | CGG | CGT | MGN |
| Lys | K | AAA | AAG | | | | | AAR |
| Met | M | ATG | | | | | | ATG |
| Ile | I | ATA | ATC | ATT | | | | ATH |
| Leu | L | CTA | CTC | CTG | CTT | TTA | TTG | YTN |
| Val | V | GTA | GTC | GTG | GTT | | | GTN |
| Phe | F | TTC | TTT | | | | | TTY |
| Tyr | Y | TAC | TAT | | | | | TAY |
| Trp | W | TGG | | | | | | TGG |
| Ter | . | TAA | TAG | TGA | | | | TRR |
| Asn\|Asp | B | | | | | | | RAY |
| Glu\|Gln | Z | | | | | | | SAR |
| Any | X | | | | | | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

One of ordinary skill in the art will also appreciate that different species can exhibit "preferential codon usage." In general, see, Grantham, et al., *Nuc. Acids Res.* 8:1893–912, 1980; Haas, et al. *Curr. Biol.* 6:315–24, 1996; Wain-Hobson, et al., *Gene* 13:355–64, 1981; Grosjean and Fiers, *Gene* 18:199–209, 1982; Holm, *Nuc. Acids Res.* 14:3075–87, 1986; Ikemura, *J. Mol. Biol.* 158:573–97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:15 serves as a template for optimizing expression of polynucleotides in various cell types and species commonly used in the art and disclosed herein. Sequences containing preferential codons can be tested and optimized for expression in various species, and tested for functionality as disclosed herein.

The highly conserved amino acids, both within and without the region of high identity, can be used as a tool to identify cystatin T polypeptides or cystatin T-like proteins. For instance, reverse transcription-polymerase chain reaction (RT-PCR) can be used to amplify sequences encoding the conserved motifs suggested by the multiple alignment from RNA obtained from a variety of tissue sources. In particular, one such probe would include a polynucleotide sequence encoding the amino acid sequence of amino acid residues 95–104 of SEQ ID NO:2. Also included in this aspect of the present invention are polypeptide probes.

Nucleic acid molecules disclosed herein can be used to detect the expression of a cystatin T gene in a biological sample. Such probe molecules include double-stranded nucleic acid molecules comprising the nucleotide sequences of SEQ ID NOs:1 or 15, or fragments thereof, as well as single-stranded nucleic acid molecules having the complement of the nucleotide sequences of SEQ ID NOs:1 or 15, or a fragment thereof. Probe molecules may be DNA, RNA, oligonucleotides, and the like.

As an illustration, suitable probes include nucleic acid molecules that bind with a portion of a cystatin T domain or motif, such as the cystatin T cysteine motif (nucleotides 325–459 of SEQ ID NO:1 or nucleotides 280–414 of SEQ ID NO:15). Other probes include nucleotides 271–459 of SEQ ID NO:1 or nucleotides 226–414 of SEQ ID NO:15.

In a basic assay, a single-stranded probe molecule is incubated with RNA, isolated from a biological sample, under conditions of temperature and ionic strength that promote base pairing between the probe and target cystatin T RNA species. After separating unbound probe from hybridized molecules, the amount of hybrids is detected.

Well-established hybridization methods of RNA detection include northern analysis and dot/slot blot hybridization (see, for example, Ausubel ibid. and Wu et al. (eds.), "Analysis of Gene Expression at the RNA Level," in *Methods in Gene Biotechnology*, pages 225–239 (CRC Press, Inc. 1997)). Nucleic acid probes can be detectably labeled with radioisotopes such as $^{32}P$ or $^{35}S$. Alternatively, cystatin T RNA can be detected with a nonradioactive hybridization method (see, for example, Isaac (ed.), *Protocols for Nucleic Acid Analysis by Nonradioactive Probes*, Humana Press, Inc., 1993). Typically, nonradioactive detection is achieved by enzymatic conversion of chromogenic or chemiluminescent substrates. Illustrative nonradioactive moieties include biotin, fluorescein, and digoxigenin.

Cystatin T oligonucleotide probes are also useful for in vivo diagnosis. As an illustration, $^{18}F$-labeled oligonucleotides can be administered to a subject and visualized by positron emission tomography (Tavitian et al., *Nature Medicine* 4:467, 1998).

Numerous diagnostic procedures take advantage of the polymerase chain reaction (PCR) to increase sensitivity of detection methods. Standard techniques for performing PCR are well-known (see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)). PCR primers can be designed to amplify a sequence encoding a particular cystatin T domain or motif, such as the cystatin T cysteine motif (encoded by about nucleotide 325–459 of SEQ ID NO:1 or nucleotides 280–414 of SEQ ID NO:15).

One variation of PCR for diagnostic assays is reverse transcriptase-PCR (RT-PCR). In the RT-PCR technique, RNA is isolated from a biological sample, reverse transcribed to cDNA, and the CDNA is incubated with cystatin T primers (see, for example, Wu et al. (eds.), "Rapid Isolation of Specific cDNAs or Genes by PCR," in *Methods in Gene Biotechnology*, CRC Press, Inc., pages 15–28, 1997). PCR is then performed and the products are analyzed using standard techniques.

As an illustration, RNA is isolated from biological sample using, for example, the guanidinium-thiocyanate cell lysis procedure described herein. Alternatively, a solid-phase technique can be used to isolate mRNA from a cell lysate. A reverse transcription reaction can be primed with the isolated RNA using random oligonucleotides, short homopolymers of dT, or cystatin T anti-sense oligomers. Oligo-dT primers offer the advantage that various mRNA nucleotide sequences are amplified that can provide control target sequences. Cystatin T sequences are amplified by the polymerase chain reaction using two flanking oligonucleotide primers that are typically at least 5 bases in length.

PCR amplification products can be detected using a variety of approaches. For example, PCR products can be fractionated by gel electrophoresis, and visualized by ethidium bromide staining. Alternatively, fractionated PCR products can be transferred to a membrane, hybridized with a detectably-labeled cystatin T probe, and examined by autoradiography. Additional alternative approaches include the use of digoxigenin-labeled deoxyribonucleic acid triphosphates to provide chemiluminescence detection, and the C-TRAK colorimetric assay.

Another approach is real time quantitative PCR (Perkin-Elmer Cetus, Norwalk, Conn.). A fluorogenic probe, consisting of an oligonucleotide with both a reporter and a quencher dye attached, anneals specifically between the forward and reverse primers. Using the 5' endonuclease activity of Taq DNA polymerase, the reporter dye is separated from the quencher dye and a sequence-specific signal is generated and increases as amplification increases. The fluorescence intensity can be continuously monitored and quantified during the PCR reaction.

Another approach for detection of cystatin T expression is cycling probe technology (CPT), in which a single-stranded DNA target binds with an excess of DNA-RNA-DNA chimeric probe to form a complex, the RNA portion is cleaved with RNase H, and the presence of cleaved chimeric probe is detected (see, for example, Beggs et al., *J. Clin. Microbiol.* 34:2985, 1996 and Bekkaoui et al., *Biotechniques* 20:240, 1996). Alternative methods for detection of cystatin T sequences can utilize approaches such as nucleic acid sequence-based amplification (NASBA), cooperative amplification of templates by cross-hybridization (CATCH), and the ligase chain reaction (LCR) (see, for example, Marshall et al., U.S. Pat. No. 5,686,272 (1997), Dyer et al., *J. Virol. Methods* 60:161, 1996; Ehricht et al., *Eur. J. Biochem.* 243:358, 1997 and Chadwick et al., *J. Virol. Methods* 70:59, 1998). Other standard methods are known to those of skill in the art.

Cystatin T probes and primers can also be used to detect and to localize cystatin T gene expression in tissue samples. Methods for such in situ hybridization are well-known to those of skill in the art (see, for example, Choo (ed.), *In Situ Hybridization Protocols,* Humana Press, Inc., 1994; Wu et al. (eds.), "Analysis of Cellular DNA or Abundance of mRNA by Radioactive In Situ Hybridization (RISH)," in *Methods in Gene Biotechnoloqy,* CRC Press, Inc., pages 259–278, 1997 and Wu et al. (eds.), "Localization of DNA or Abundance of mRNA by Fluorescence In Situ Hybridization (RISH)," in *Methods in Gene Biotechnology,* CRC Press, Inc., pages 279–289, 1997).

Various additional diagnostic approaches are well-known to those of skill in the art (see, for example, Mathew (ed.), *Protocols in Human Molecular Genetics* Humana Press, Inc., 1991; Coleman and Tsongalis, *Molecular Diagnostics,* Humana Press, Inc., 1996 and Elles, *Molecular Diagnosis of Genetic Diseases,* Humana Press, Inc., 1996).

The chromosomal localization of the cystatin T gene can be determined using methods known in the art. The precise knowledge of a gene's position can be useful in a number of ways including: 1) determining if a sequence is part of an existing contig and obtaining additional surrounding genetic sequences in various forms such as YAC-, BAC- or cDNA clones, 2) providing a possible candidate gene for an inheritable disease which shows linkage to the same chromosomal region, and 3) for cross-referencing model organisms which may be beneficial in helping to determine what function a particular gene might have.

Known members of the type 2 cystatins are clustered on chromosome 20. Cystatin C (CST3) and D (CST5) are found in the human 20p11 region, and cystatin SN (CST1) and cystatin SA (CST2) are found in the human 20q13.3 region. Cystatin T has been mapped to mouse chromosome 2 in the region syntenic with the 20p11.2 region of human chromosome 20.

The present invention provides reagents for use in diagnostic applications. For example, the cystatin T gene, a probe comprising cystatin T DNA or RNA, or a subsequence thereof can be used to determine if the cystatin T gene is present on a specific chromosome or if a mutation has occurred. Detectable chromosomal aberrations at the cystatin T gene locus include, but are not limited to, aneuploidy, gene copy number changes, insertions, deletions, restriction site changes and rearrangements. These aberrations can occur within the coding sequence, within introns, or within flanking sequences, including upstream promoter and regulatory regions, and may be manifested as physical alterations within a coding sequence or changes in gene expression level.

In general, these diagnostic methods comprise the steps of (a) obtaining a genetic sample from a patient; (b) incubating the genetic sample with a polynucleotide probe or primer as disclosed above, under conditions wherein the polynucleotide will hybridize to complementary polynucleotide sequence, to produce a first reaction product; and (iii) comparing the first reaction product to a control reaction product. A difference between the first reaction product and the control reaction product is indicative of a genetic abnormality in the patient. Genetic samples for use within the present invention include genomic DNA, cDNA, and RNA. The polynucleotide probe or primer can be RNA or DNA, and will comprise a portion of SEQ ID NO:1, the complement of SEQ ID NO:1, or an RNA equivalent thereof. Suitable assay methods in this regard include molecular genetic techniques known to those in the art, such as restriction fragment length polymorphism (RFLP) analysis, short tandem repeat (STR) analysis employing PCR techniques, ligation chain reaction (Barany, *PCR Methods and Applications* 1:5–16, 1991), ribonuclease protection assays, and other genetic linkage analysis techniques known in the art (Sambrook et al., ibid.; Ausubel et. al., ibid.; Marian, *Chest* 108:255–65, 1995). Ribonuclease protection assays (see, e.g., Ausubel et al., ibid., ch. 4) comprise the hybridization of an RNA probe to a patient RNA sample, after which the reaction product (RNA-RNA hybrid) is exposed to RNase. Hybridized regions of the RNA are protected from digestion. Within PCR assays, a patient's genetic sample is incubated with a pair of polynucleotide primers, and the region between the primers is amplified and recovered. Changes in size or amount of recovered product are indicative of mutations in the patient. Another PCR-based technique that can be employed is single strand conformational polymorphism (SSCP) analysis (Hayashi, *PCR Methods and Applications* 1:34–8, 1991).

Within preferred embodiments of the invention the isolated polynucleotides will hybridize to similar sized regions of SEQ ID NO:1, other polynucleotide probes, primers, fragments and sequences recited herein or sequences complementary thereto. Polynucleotide hybridization is well known in the art and widely used for many applications, see for example, Sambrook et al., *Molecular Cloning: A Laboratory Manual, Second Edition,* Cold Spring Harbor, N.Y., 1989; Ausubel et al., eds., *Current Protocols in Molecular Biology,* John Wiley and Sons, Inc., N.Y., 1987; Berger and Kimmel, eds., Guide to Molecular Cloning Techniques, *Methods in Enzymology,* volume 152, 1987 and Wetmur, *Crit. Rev. Biochem. Mol. Biol.* 26:227–59, 1990. Polynucleotide hybridization exploits the ability of single stranded complementary sequences to form a double helix hybrid. Such hybrids include DNA-DNA, RNA-RNA and DNA-RNA.

Hybridization will occur between sequences which contain some degree of complementarity. Hybrids can tolerate mismatched base pairs in the double helix, but the stability of the hybrid is influenced by the degree of mismatch. The $T_m$ of the mismatched hybrid decreases by 1° C. for every 1–1.5% base pair mismatch. Varying the stringency of the hybridization conditions allows control over the degree of mismatch that will be present in the hybrid. The degree of stringency increases as the hybridization temperature increases and the ionic strength of the hybridization buffer decreases. Stringent hybridization conditions encompass temperatures of about 5–25° C. below the thermal melting point ($T_m$) of the hybrid and a hybridization buffer having up to 1 M $Na^+$. Higher degrees of stringency at lower temperatures can be achieved with the addition of formamide which reduces the $T_m$ of the hybrid about 1° C. for each 1% formamide in the buffer solution. Generally, such stringent conditions encompass temperatures of 20–70° C. and a hybridization buffer containing up to 6×SSC and 0–50% formamide. A higher degree of stringency can be achieved at temperatures of from 40–70° C. with a hybridization buffer having up to 4×SSC and from 0–50% formamide. Highly stringent conditions typically encompass temperatures of 42–70° C. with a hybridization buffer having up to 1×SSC and 0–50% formamide. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes.

The above conditions are meant to serve as a guide and it is well within the abilities of one skilled in the art to adapt these conditions for use with a particular polypeptide hybrid. The $T_m$ for a specific target sequence is the temperature (under defined conditions) at which 50% of the target sequence will hybridize to a perfectly matched probe sequence. Those conditions which influence the $T_m$ include, the size and base pair content of the polynucleotide probe, the ionic strength of the hybridization solution, and the presence of destabilizing agents in the hybridization solution. Numerous equations for calculating $T_m$ are known in the art, see for example (Sambrook et al., ibid.; Ausubel et al., ibid.; Berger and Kimmel, ibid. and Wetmur, ibid.) and are specific for DNA, RNA and DNA-RNA hybrids and polynucleotide probe sequences of varying length. Sequence analysis software such as Oligo 4.0 (publicly available shareware) and Primer Premier (PREMIER Biosoft International, Palo Alto, Calif.) as well as sites on the Internet, are available tools for analyzing a given sequence and calculating $T_m$ based on user defined criteria. Such programs can also analyze a given sequence under defined conditions and suggest suitable probe sequences. Typically, hybridization of longer polynucleotide sequences, >50 bp, is done at temperatures of about 20–25° C. below the calculated $T_m$. For smaller probes, <50 bp, hybridization is typically carried out at the $T_m$ or 5–10° C. below. This allows for the maximum rate of hybridization for DNA-DNA and DNA-RNA hybrids.

The length of the polynucleotide sequence influences the rate and stability of hybrid formation. Smaller probe sequences, <50 bp, come to equilibrium with complementary sequences rapidly, but may form less stable hybrids. Incubation times of anywhere from minutes to hours can be used to achieve hybrid formation. Longer probe sequences come to equilibrium more slowly, but form more stable complexes even at lower temperatures. Incubations are allowed to proceed overnight or longer. Generally, incubations are carried out for a period equal to three times the calculated Cot time. Cot time, the time it takes for the polynucleotide sequences to reassociate, can be calculated for a particular sequence by methods known in the art.

The base pair composition of polynucleotide sequence will effect the thermal stability of the hybrid complex, thereby influencing the choice of hybridization temperature and the ionic strength of the hybridization buffer. A-T pairs are less stable than G-C pairs in aqueous solutions containing NaCl. Therefore, the higher the G-C content, the more stable the hybrid. Even distribution of G and C residues within the sequence also contribute positively to hybrid stability. Base pair composition can be manipulated to alter the $T_m$ of a given sequence, for example, 5-methyldeoxycytidine can be substituted for deoxycytidine and 5-bromodeoxyuridine can be substituted for thymidine to increase the $T_m$. 7-deazo-2'-deoxyguanosine can be substituted for guanosine to reduce dependence on $T_m$.

Ionic concentration of the hybridization buffer also effects the stability of the hybrid. Hybridization buffers generally contain blocking agents such as Denhardt's solution (Sigma Chemical Co., St. Louis, Mo.), denatured salmon sperm DNA, tRNA, milk powders (BLOTTO), heparin or SDS, and a $Na^+$ source, such as SSC (1×SSC: 0.15 M NaCl, 15 mM sodium citrate) or SSPE (1×SSPE: 1.8 M NaCl, 10 mM $NaH_2PO_4$, 1 mM EDTA, pH 7.7). By decreasing the ionic concentration of the buffer, the stability of the hybrid is increased. Typically, hybridization buffers contain from between 10 mM–1 M $Na^+$. Premixed hybridization solutions are also available from commercial sources such as Clontech Laboratories (Palo Alto, Calif.) and Promega Corporation (Madison, Wis.) for use according to manufacturer's instruction. Addition of destabilizing or denaturing agents such as formamide, tetralkylammonium salts, guanidinium cations or thiocyanate cations to the hybridization solution will alter the $T_m$ of a hybrid. Typically, formamide is used at a concentration of up to 50% to allow incubations to be carried out at more convenient and lower temperatures. Formamide also acts to reduce non-specific background when using RNA probes.

As previously noted, the isolated polynucleotides of the present invention include DNA and RNA. Methods for isolating DNA and RNA are well known in the art. It is generally preferred to isolate RNA from testis, although DNA can also be prepared using RNA from other tissues or isolated as genomic DNA. Total RNA can be prepared using guanidine HCl extraction followed by isolation by centrifugation in a CsCl gradient (Chirgwin et al., *Biochemistry* 18:52–94, 1979). Poly $(A)^+$ RNA is prepared from total RNA using the method of Aviv and Leder (*Proc. Natl. Acad. Sci. USA* 69:1408–1412, 1972). Complementary DNA (cDNA) is prepared from poly$(A)^+$RNA using known methods. Polynucleotides encoding cystatin T polypeptides are then identified and isolated by, for example, hybridization or PCR.

The polynucleotides of the present invention can also be synthesized using automated equipment. The current method of choice is the phosphoramidite method. If chemically synthesized double stranded DNA is required for an application such as the synthesis of a gene or a gene fragment, then each complementary strand is made separately. The production of short genes (60 to 80 bp) is technically straightforward and can be accomplished by synthesizing the complementary strands and then annealing them. For the production of longer genes (>300 bp), however, special strategies must be invoked, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. Gene synthesis methods are well known in the art. See, for example, Glick and Pasternak, *Molecular Biotechnology, Principles & Applications of Recombinant DNA*, ASM Press, Washington, D.C., 1994; Itakura et al., *Annu. Rev. Biochem.* 53: 323–56, 1984; and Climie et al., *Proc. Natl. Acad. Sci. USA* 87:633–7, 1990.

The present invention further provides counterpart polypeptides and polynucleotides from other species (orthologs). These species include, but are not limited to, mammalian, avian, amphibian, reptile, fish, insect, and other vertebrate and invertebrate species. Of particular interest are cystatin T polypeptides from other mammalian species, including human, rat, porcine, ovine, bovine, canine, feline, equine and other primate proteins. Species homologs of the human proteins can be cloned using information and compositions provided by the present invention in combination with conventional cloning techniques. For example, a cDNA can be cloned using mRNA obtained from a tissue or cell type that expresses the protein. Suitable sources of mRNA can be identified by probing Northern blots with probes designed from the sequences disclosed herein. A library is then prepared from mRNA of a positive tissue of cell line. A cystatin T polypeptide-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the sequences disclosed herein. Within an additional method, the cDNA library can be used to transform or transfect host cells, and expression of the cDNA of interest can be detected with an antibody to cystatin T polypeptide. Similar techniques can also be applied to the isolation of genomic clones.

Alternate species polypeptides of cystatin T may have importance therapeutically. It has been demonstrated that in some cases use of a non-native protein, i.e., protein from a different species, can be more potent than the native protein. For example, salmon calcitonin has been shown to be considerably more effective in arresting bone resorption than human forms of calcitonin. There are several hypotheses as to why salmon calcitonin is more potent than human calcitonin in treatment of osteoporosis. These hypotheses include: 1) salmon calcitonin is more resistant to degradation; 2) salmon calcitonin has a lower metabolic clearance rate (MCR); and 3) salmon calcitonin may have a slightly different conformation, resulting in a higher affinity for bone receptor sites. Another example is found in the β-endorphin family (Ho et al., *Int. J. Peptide Protein Res.* 29:521–24, 1987). Studies have demonstrated that the peripheral opioid activity of camel, horse, turkey and ostrich β-endorphins is greater than that of human β-endorphins when isolated guinea pig ileum was electrostimulated and contractions were measured. Vas deferens from rat, mouse and rabbit were assayed as well. In the rat vas deferens model, camel and horse β-endorphins showed the highest relative potency. Synthesized rat relaxin was as active as human and porcine relaxin in the mouse symphysis pubis assay (Bullesbach and Schwabe, *Eur. J. Biochem.* 241:533–7, 1996). Thus, the mouse cystatin T molecule of the present invention may have higher potency than the human endogenous molecule in human cells, tissues and recipients.

Those skilled in the art will recognize that the sequences disclosed in SEQ ID NO:1 and SEQ ID NO:2 represent a single allele of the mouse cystatin T gene and polypeptide, and that allelic variation and alternative splicing are expected to occur. Allelic variants can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention as are proteins which are allelic variants of SEQ ID NO:2. cDNAs generated from alternatively spliced mRNAs, which retain the properties of the cystatin T polypeptide are included within the scope of the present invention, as are polypeptides encoded by such cDNAs and mRNAs. Allelic variants and splice variants of these sequences can be cloned by probing CDNA or genomic libraries from different individuals or tissues according to standard procedures known in the art.

The present invention also provides isolated cystatin T polypeptides that are substantially homologous to the polypeptides of SEQ ID NO:2 and their species orthologs. The term "substantially homologous" is used herein to denote polypeptides having 50%, preferably 60%, more preferably at least 80%, sequence identity to the sequences shown in SEQ ID NO:2 or their orthologs. Such polypeptides will more preferably be at least 90% identical, and most preferably 95% or more identical to SEQ ID NO:2 or its orthologs. Percent sequence identity is determined by conventional methods. See, for example, Altschul et al., *Bull. Math. Bio.* 48: 603–66, 1986 and Henikoff and Henikoff, *Proc. Natl. Acad. Sci. USA* 89:10915–9, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

TABLE 3

|   | A  | R  | N  | D  | C  | Q  | E  | G  | H  | I  | L  | K  | M  | F  | P  | S  | T  | W  | Y | V |
|---|----|----|----|----|----|----|----|----|----|----|----|----|----|----|----|----|----|----|---|---|
| A | 4  |    |    |    |    |    |    |    |    |    |    |    |    |    |    |    |    |    |   |   |
| R | -1 | 5  |    |    |    |    |    |    |    |    |    |    |    |    |    |    |    |    |   |   |
| N | -2 | 0  | 6  |    |    |    |    |    |    |    |    |    |    |    |    |    |    |    |   |   |
| D | -2 | -2 | 1  | 6  |    |    |    |    |    |    |    |    |    |    |    |    |    |    |   |   |
| C | 0  | -3 | -3 | -3 | 9  |    |    |    |    |    |    |    |    |    |    |    |    |    |   |   |
| Q | -1 | 1  | 0  | 0  | -3 | 5  |    |    |    |    |    |    |    |    |    |    |    |    |   |   |
| E | -1 | 0  | 0  | 2  | -4 | 2  | 5  |    |    |    |    |    |    |    |    |    |    |    |   |   |
| G | 0  | -2 | 0  | -1 | -3 | -2 | -2 | 6  |    |    |    |    |    |    |    |    |    |    |   |   |
| H | -2 | 0  | 1  | -1 | -3 | 0  | 0  | -2 | 8  |    |    |    |    |    |    |    |    |    |   |   |
| I | -1 | -3 | -3 | -3 | -1 | -3 | -3 | -4 | -3 | 4  |    |    |    |    |    |    |    |    |   |   |
| L | -1 | -2 | -3 | -4 | -1 | -2 | -3 | -4 | -3 | 2  | 4  |    |    |    |    |    |    |    |   |   |
| K | -1 | 2  | 0  | -1 | -3 | 1  | 1  | -2 | -1 | -3 | -2 | 5  |    |    |    |    |    |    |   |   |
| M | -1 | -1 | -2 | -3 | -1 | 0  | -2 | -3 | -2 | 1  | 2  | -1 | 5  |    |    |    |    |    |   |   |
| F | -2 | -3 | -3 | -3 | -2 | -3 | -3 | -3 | -1 | 0  | 0  | -3 | 0  | 6  |    |    |    |    |   |   |
| P | -1 | -2 | -2 | -1 | -3 | -1 | -1 | -2 | -2 | -3 | -3 | -1 | -2 | -4 | 7  |    |    |    |   |   |
| S | 1  | -1 | 1  | 0  | -1 | 0  | 0  | 0  | -1 | -2 | -2 | 0  | -1 | -2 | -1 | 4  |    |    |   |   |
| T | 0  | -1 | 0  | -1 | -1 | -1 | -1 | -2 | -2 | -1 | -1 | -1 | -1 | -2 | -1 | 1  | 5  |    |   |   |
| W | -3 | -3 | -4 | -4 | -2 | -2 | -3 | -2 | -2 | -3 | -2 | -3 | -1 | 1  | -4 | -3 | -2 | 11 |   |   |
| Y | -2 | -2 | -2 | -3 | -2 | -1 | -2 | -3 | 2  | -1 | -1 | -2 | -1 | 3  | -3 | -2 | -2 | 2  | 7 |   |
| V | 0  | -3 | -3 | -3 | -1 | -2 | -2 | -3 | -3 | 3  | 1  | -2 | 1  | -1 | -2 | -2 | 0  | -3 | -1| 4 |

Sequence identity of polynucleotide molecules is determined by similar methods using a ratio as disclosed above.

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant cystatin T. The FASTA algorithm is described by Pearson and Lipman, *Proc. Nat. Acad. Sci. USA* 85:2444, 1988, and by Pearson, *Meth. Enzymol.* 183:63, 1990.

Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444, 1970); Sellers, *SIAM J. Appl. Math.* 26:787, 1974), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63, 1990.

FASTA can also be used to determine the sequence identity of nucleic acid molecules using a ratio as disclosed above. For nucleotide sequence comparisons, the ktup value can range between one to six, preferably from three to six, most preferably three, with other parameters set as default.

The present invention includes nucleic acid molecules that encode a polypeptide having one or more conservative amino acid changes, compared with the amino acid sequence of SEQ ID NO:2. The BLOSUM62 table is an amino acid substitution matrix derived from about 2,000 local multiple alignments of protein sequence segments, representing highly conserved regions of more than 500 groups of related proteins (Henikoff and Henikoff, *Proc. Nat. Acad. Sci. USA* 89:10915, 1992). Accordingly, the BLOSUM62 substitution frequencies can be used to define conservative amino acid substitutions that may be introduced into the amino acid sequences of the present invention. As used herein, the language "conservative amino acid substitution" refers to a substitution represented by a BLOSUM62 value of greater than −1. For example, an amino acid substitution is conservative if the substitution is characterized by a BLOSUM62 value of 0, 1, 2, or 3. Preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Substantially homologous proteins and polypeptides are characterized as having one or more amino acid substitutions, deletions or additions. These changes are preferably of a minor nature, that is conservative amino acid substitutions (see Table 4) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or an affinity tag. Polypeptides comprising affinity tags can further comprise a proteolytic cleavage site between the cystatin T polypeptide and the affinity tag. Preferred such sites include thrombin cleavage sites and factor Xa cleavage sites.

TABLE 4

| Conservative amino acid substitutions | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

In addition to the 20 standard amino acids, non-standard amino acids (such as 4-hydroxyproline, 6-N-methyl lysine, 2-aminoisobutyric acid, isovaline and a-methyl serine) may be substituted for amino acid residues of cystatin T polypeptides of the present invention. A limited number of non-conservative amino acids, amino acids that are not encoded by the genetic code, and unnatural amino acids may be substituted for cystatin T polypeptide amino acid residues. The proteins of the present invention can also comprise non-naturally occurring amino acid residues.

Non-naturally occurring amino acids include, without limitation, trans-3-methylproline, 2,4-methano-proline, cis-4-hydroxyproline, trans-4-hydroxyproline, N-methylglycine, allo-threonine, methylthreonine, hydroxyethylcysteine, hydroxyethyl-homocysteine, nitroglutamine, homoglutamine, pipecolic acid, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–9, 1993; and Chung et al., *Proc. Natl. Acad. Sci. USA* 90:10145–9, 1993). In a second method, translation is carried out in Xenopus oocytes by microinjection of mutated mRNA and chemically aminoacylated suppressor tRNAs (Turcatti et al., *J. Biol. Chem.* 271:19991–8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

A limited number of non-conservative amino acids, amino acids that are not encoded by the genetic code, non-naturally occurring amino acids, and unnatural amino acids may be substituted for cystatin T amino acid residues.

Essential amino acids in the cystatin T polypeptides of the present invention can be identified according to procedures known in the art, such as site-directed mutagenesis or alanine-scanning mutagenesis (Cunningham and Wells, *Science* 244: 1081–5, 1989). Site directed mutagenesis of cystatin C to generate cystatin C variants is discussed in Hall et al., *Biochem. J.* 291: 123–9, 1993. In the latter technique, single alanine mutations are introduced at every residue in the molecule, and the resultant mutant molecules are tested for biological activity (e.g., modulating spermatogenesis) to identify amino acid residues that are critical to the activity of the molecule. See also, Hilton et al., *J. Biol. Chem.* 271:4699–708, 1996. Sites of biological interaction, such as cystatin T polypeptide-cysteine proteinase inhibitor-enzyme interaction, can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–12, 1992; Smith et al., *J. Mol. Biol.* 224:899–904, 1992; Wlodaver et al., *FEBS Lett.* 309:59–64, 1992. The identities of essential amino acids can also be inferred from analysis of homologies with related cystatin family members.

Multiple amino acid substitutions can be made and tested using known methods of mutagenesis and screening, such as those disclosed by Reidhaar-Olson and Sauer (*Science* 241:53–7, 1988) or Bowie and Sauer (*Proc. Natl. Acad. Sci. USA* 86:2152–6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–7, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed cystatin T DNA and polypeptide sequences can be generated through DNA shuffling as disclosed by Stemmer, *Nature* 370:389–91, 1994, Stemmer, *Proc. Natl. Acad. Sci. USA* 91:10747–51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed above can be combined with high-throughput, automated screening methods to detect activity of cloned, mutagenized polypeptides in host cells. Mutagenized DNA molecules that encode active polypeptides (e.g., cysteine protease inhibition or binding) can be recovered from the host cells and rapidly sequenced using modern equipment. These methods allow the rapid determination of the importance of individual amino acid residues in a polypeptide of interest, and can be applied to polypeptides of unknown structure.

Polypeptides of the present invention comprise at least 6, preferably at least 9, more preferably at least 15 contiguous amino acid residues of SEQ ID NO:2. Within certain embodiments of the invention, the polypeptides comprise 20, 30, 40, 50 or more contiguous residues of SEQ ID NO:2, up to the entire predicted mature polypeptide (residues 21–141 of SEQ ID NO:2) or the primary translation product (residues 1 to 141 of SEQ ID NO:2). As disclosed in more detail below, these polypeptides can further comprise additional, non-cystatin T, polypeptide sequence(s). Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Natl. Acad. Sci. USA* 81:3998, 1983).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660, 1983). Accordingly, antigenic epitope-bearing peptides and polypeptides of the present invention are useful to raise antibodies that bind with the polypeptides described herein.

Such epitope-bearing peptides and polypeptides can be produced by fragmenting a cystatin T polypeptide, or by chemical peptide synthesis, as described herein. Moreover, epitopes can be selected by phage display of random peptide libraries (see, for example, Lane and Stephen, *Curr. Opin. Immunol.* 5:268, 1993), and Cortese et al., *Curr. Opin. Biotechnol.* 7:616, 1996). Standard methods for identifying epitopes and producing antibodies from small peptides that comprise an epitope are described, for example, by Mole, "Epitope Mapping," in *Methods in Molecular Bioloqy*, Vol. 10, Manson (ed.), pages 105–116 (The Humana Press, Inc. 1992), Price, ※ Production and Characterization of Synthetic Peptide-Derived Antibodies," in *Monoclonal Antibodies: Production, Engineering, and Clinical Application*, Ritter and Ladyman (eds.), pages 60–84 (Cambridge University Press 1995), and Coligan et al. (eds.), *Current Protocols in Immunology*, pages 9.3.1–9.3.5 and pages 9.4.1–9.4.11 (John Wiley & Sons 1997).

Antibodies that recognize short, linear epitopes are particularly useful in analytic and diagnostic applications that employ denatured protein, such as Western blotting (Tobin, *Proc. Natl. Acad. Sci. USA* 76:4350–6, 1979), or in the analysis of fixed cells or tissue samples. Antibodies to linear epitopes are also useful for detecting fragments of cystatin T, such as might occur in body fluids or cell culture media.

For any cystatin T polypeptide, including variants and fusion proteins, one of ordinary skill in the art can readily generate a fully degenerate polynucleotide sequence encoding that variant using the information set forth in Tables 1 and 2 above. Moreover, those of skill in the art can use standard software to devise cystatin T variants based upon the nucleotide and amino acid sequences described herein. Accordingly, the present invention includes a computer-readable medium encoded with a data structure that provides at least one of the following sequences: SEQ ID NO:1, SEQ ID NO:2 and SEQ ID NO:15. Suitable forms of computer-readable media include magnetic media and optically-readable media. Examples of magnetic media include a hard or fixed drive, a random access memory (RAM) chip, a floppy disk, digital linear tape (DLT), a disk cache, and a ZIP disk. Optically readable media are exemplified by compact discs (e.g., CD-read only memory (ROM), CD-rewritable (RW), and CD-recordable), and digital versatile/video discs (DVD) (e.g., DVD-ROM, DVD-RAM, and DVD+RW).

Using the methods discussed above, one of ordinary skill in the art can identify and/or prepare a variety of polypeptides that are substantially homologous to residues 21 to 141 of SEQ ID NO:2 or allelic variants thereof and retain the cysteine protease inhibitory or binding properties of the wild-type protein. Such polypeptides may include additional amino acids or domains from other members of the cystatin superfamily, affinity tags or the like. Cystatin T polypeptide or fragment fusion constructs, containing functional domains of other members of the cystatin superfamily, constitute hybrid cysteine proteinase inhibitors exhibiting modified cysteine proteinase inhibitory or binding capabilities.

Potential single site mutations in the structure of cystatin T polypeptides of the present invention can also be identified by structural analysis. An alignment of cystatin T with murine and human CRES (SEQ ID NOs:3 and 4), murine and human cystatin C (SEQ ID NOs: 5 and 6), human cystatin D (SEQ ID NO:7), human cystatin E (SEQ ID NO:8), human cystatin F (SEQ ID NO:9), human cystatin M (SEQ ID NO:10), human cystatin S (SEQ ID NO:12) and human cystatin SA-I (SEQ ID NO:13) can be used to identify such amino acid residues. Amino acid residues 43 (Val), 56 (Asn), 76 Gln), 83 (Tyr), 94 (Cys), 96 (Lys), 104 (Cys), 118 (Cys), 127 (Trp) and 138 (Cys) of SEQ ID NO:2 are conserved between these members of the cystatin family. At position 8 of SEQ ID NO:2, most members of the cystatin protein family have either Lys or Ala at this position. At position 47 of SEQ ID NO:2, members of the cystatin family of proteins have either Ala or Cys at that position. At position 51 of SEQ ID NO:2, members of the cystatin family of proteins have either Ala or Ser at that position. At position 61 of SEQ ID NO:2, members of the cystatin family of proteins have either Asp or Ser at that position. At position 63 of SEQ ID NO:2, members of the cystatin family of proteins have either Tyr or Phe at that position. At position 73 of SEQ ID NO:2, members of the cystatin family of proteins have either Ser or Ala at that position. At position 87 of SEQ ID NO:2, members of the cystatin family of proteins have either Val or Met at that position. At position 91 of SEQ ID NO:2, members of the cystatin family of proteins have either Arg or Ser at that position. At position 92 of SEQ ID NO:2, members of the cystatin family of proteins have either Thr or Ser at that position. At position 120 of SEQ ID NO:2, members of the cystatin family of proteins have either Phe or Ser at that position. Suggested mutations for cystatin T polypeptides of the present invention therefore include substitution of the alternate amino acid residue at one or more positions. Additionally, such substitution could include conservative substitutions as shown in Table 4.

Such polypeptides may also include additional polypeptide segments as generally disclosed above. For any cystatin T polypeptide, including variants and fusion proteins, one of ordinary skill in the art can readily generate a fully degenerate polynucleotide sequence encoding that variant using the information set forth in Tables 1 and 2 above.

The polypeptides of the present invention, including full-length proteins, fragments thereof and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual,* 2nd ed., Cold Spring Harbor Laboratory Press, Cold Spring Harbor, N.Y., 1989, and Ausubel et al. (eds.), *Current Protocols in Molecular Biology,* John Wiley and Sons, Inc., NY, 1987.

In general, a DNA sequence encoding a cystatin T polypeptide of the present invention is operably linked to other genetic elements required for its expression, generally including a transcription promoter and terminator within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a cystatin T polypeptide into the secretory pathway of a host cell, a secretory signal sequence (also known as a signal sequence, leader sequence, prepro sequence or pre sequence) is provided in the expression vector. The secretory signal sequence may be that of the cystatin T polypeptide, or may be derived from another secreted protein (e.g., t-PA) or synthesized de novo. The secretory signal sequence is joined to the cystatin T polypeptide-encoding DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Alternatively, the secretory signal sequence contained in the polypeptides of the present invention is used to direct other polypeptides into the secretory pathway. The present invention provides for such fusion polypeptides. A signal fusion polypeptide can be made wherein a secretory signal sequence derived from amino acid residues 1–20 of SEQ ID NO:2 is be operably linked to another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein, such as a receptor. Such fusions may be used in vivo or in vitro to direct peptides through the secretory pathway. The invention provides constructs wherein the secretory signal sequence portion of the cystatin T polypeptide (amino acids 1–20 of SEQ ID NO: 2) is employed to direct the secretion of an alternative protein by analogous methods.

Cultured mammalian cells are also suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982), DEAE-dextran mediated transfection (Ausubel et al., eds., *Current Protocols in Molecular Biology,* John Wiley and Sons, Inc., NY, 1987), liposome-mediated transfection (Hawley-Nelson et al., *Focus* 15:73, 1993; Ciccarone et al., *Focus* 15:80, 1993), and viral vectors (Miller and Rosman, *BioTechniques* 7:980–90, 1989; Wang and Finer, *Nature Med.* 2:714–6, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci. (Bangalore)* 11:47–58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). DNA encoding the cystatin T polypeptide is inserted into the baculoviral genome in place of the AcNPV polyhedrin gene coding sequence by one of two methods. The first is the traditional method of homologous DNA recombination between wild-type AcNPV and a transfer vector containing the cystatin T flanked by AcNPV sequences. Suitable insect cells, e.g. SF9 cells, are infected with wild-type AcNPV and transfected with a transfer vector comprising a cystatin T polynucleotide operably linked to an AcNPV polyhedrin gene promoter, terminator, and flanking sequences. See, King and Possee, *The Baculovirus Expression System: A Laboratory Guide,* London, Chapman & Hall; O'Reilly et al., *Baculovirus Expression Vectors: A Laboratory Manual,* New York, Oxford University Press., 1994; and, Richardson (Ed.), *Baculovirus Expression Protocols. Methods in Molecular Biology,* Totowa, N.J., Humana Press, 1995. Natural recombination within an insect cell will result in a recombinant baculovirus which contains cystatin T driven by the polyhedrin promoter. Recombinant viral stocks are made by methods commonly used in the art.

The second method of making recombinant baculovirus utilizes a transposon-based system described by Luckow et al. (*J. Virol.* 67:4566–79, 1993). This system is sold in the Bac-to-Bac kit (Life Technologies, Rockville, Md.). This system utilizes a transfer vector, pFastBac1™ (Life Technologies) containing a Tn7 transposon to move the DNA encoding the cystatin T polypeptide into a baculovirus genome maintained in *E. coli* as a large plasmid called a "bacmid." The pFastBac1™ transfer vector utilizes the AcNPV polyhedrin promoter to drive the expression of the gene of interest, in this case cystatin T. However, pFastBac1™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, Hill-Perkins and Possee, *J. Gen. Virol.* 71:971–6, 1990; Bonning et al., *J. Gen. Virol.* 75:1551–6, 1994; and, Chazenbalk and Rapoport, *J. Biol. Chem.* 270:1543–9, 1995. In such transfer vector constructs, a short or long version of the basic protein promoter can be used. Moreover, transfer vectors can be constructed which replace the native cystatin T secretory signal sequences with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native cystatin T secretory signal sequence. In addition, transfer vectors can include an in-frame fusion with DNA encoding an epitope tag at the C- or N-terminus of the expressed cystatin T polypeptide, for example, a Glu-Glu epitope tag (Grussenmeyer et al., *Proc. Natl. Acad. Sci.* 82:7952–4, 1985). Using a technique known in the art, a transfer vector containing cystatin T is transformed into *E. coli* and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses cystatin T is subsequently produced. Recombinant viral stocks are made by methods commonly used the art.

The recombinant virus is used to infect host cells, typically a cell line derived from the fall armyworm, *Spodoptera*

*frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately $2-5\times10^5$ cells to a density of $1-2\times10^6$ cells at which time a recombinant viral stock is added at a multiplicity of infection (MOI) of 0.1 to 10, more typically near 3. The recombinant virus-infected cells typically produce the recombinant cystatin T polypeptide at 12–72 hours post-infection and secrete it with varying efficiency into the medium. The culture is usually harvested 48 hours post-infection. Centrifugation is used to separate the cells from the medium (supernatant). The supernatant containing the cystatin T polypeptide is filtered through micropore filters, usually 0.45 $\mu$m pore size. Procedures used are generally described in available laboratory manuals (King and Possee, ibid.; O'Reilly et al., ibid.; Richardson, ibid.). Subsequent purification of the cystatin T polypeptide from the supernatant can be achieved using methods described herein.

Fungal cells, including yeast cells, can also be used within the present invention. Yeast species of particular interest in this regard include *Saccharomyces cerevisiae, Pichia pastoris,* and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *S. cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, P. pastoris, P. methanolica, P. guillermondii* and *Candida maltosa* are known in the art. See, for example, Gleeson et al., *J. Gen. Microbiol.* 132:3459–65, 1986 and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2) Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Prokaryotic host cells, including strains of the bacteria *Escherichia coli*, Bacillus and other genera are also useful host cells within the present invention. Techniques for transforming these hosts and expressing foreign DNA sequences cloned therein are well known in the art (see, e.g., Sambrook et al., ibid.). When expressing a cystatin T polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2%

D-glucose, 2% BaCto™ Peptone (Difco Laboratories, Detroit, Mich.), 1% Bacto™ yeast extract (Difco Laboratories), 0.004% adenine and 0.006% L-leucine).

Expressed recombinant cystatin T polypeptides (or chimeric cystatin T polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable anion exchange media include derivatized dextrans, agarose, cellulose, polyacrylamide, specialty silicas, and the like. PEI, DEAE, QAE and Q derivatives are preferred, with DEAE Fast-Flow Sepharose (Pharmacia, Piscataway, N.J.) being particularly preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods,* Pharmacia LKB Biotechnology, Uppsala, Sweden, 1988.

The polypeptides of the present invention can be isolated by exploitation of their structural features. For example, immobilized metal ion adsorption (IMAC) chromatography can be used to purify histidine-rich proteins or proteins having a His-tag. Briefly, a gel is first charged with divalent metal ions to form a chelate (E. Sulkowski, *Trends in Biochem.* 3:1–7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.,* Vol. 182, "Guide to Protein Purification", Deutscher, (ed.), Acad. Press, San Diego, 1990, pp.529–39). Within additional embodiments of the invention, a fusion of the polypeptide of interest and an affinity tag (e.g., polyhistidine, maltose-binding protein, Glu-Glu tag, FLAG tag, an immunoglobulin domain) may be constructed to facilitate purification.

Protein refolding (and optionally reoxidation) procedures may be advantageously used. It is preferred to purify the protein to >80% purity, more preferably to >90% purity, even more preferably >95%, and particularly preferred is a pharmaceutically pure state, that is greater than 99.9% pure with respect to contaminating macromolecules, particularly other proteins and nucleic acids, and free of infectious and pyrogenic agents. Preferably, a purified protein is substantially free of other proteins, particularly other proteins of animal origin.

Cystatin T polypeptides or fragments thereof may also be prepared through chemical synthesis. Cystatin T polypeptides may be monomers or multimers; glycosylated or non-glycosylated; pegylated or non-pegylated; and may or may not include an initial methionine amino acid residue.

A cystatin T ligand-binding polypeptide can also be used for purification of ligand. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing ligand are passed through the column one or more times to allow ligand to bind to the receptor polypeptide. The ligand is then eluted using changes in salt concentration, chaotropic agents (guanidine HCl), or pH to disrupt ligand-receptor binding.

An assay system that uses a ligand-binding receptor (or an antibody, one member of a complement/anti-complement pair) or a binding fragment thereof, and a commercially available biosensor instrument (BIAcore™, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229–40, 1991 and Cunningham and Wells, *J. Mol. Biol.* 234:554–63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding. As used herein, the term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9 \, M^{-1}$.

The ability of polypeptides of the present invention to stimulate proliferation or differentiation of testicular cells can be measured using cultured testicular cells or in vivo by administering molecules of the present invention to the appropriate animal model. Cultured testicular cells include dolphin DB1.Tes cells (CRL-6258); mouse GC-1 spg cells (CRL-2053); TM3 cells (CRL-1714); TM4 cells (CRL-1715); MLTC-1 (CRL-2065); I-10 (CCL-83); and pig ST cells (CRL-1746), available from American Type Culture Collection, 12301 Parklawn Drive, Rockville, Md. Assays measuring cell proliferation or differentiation are well known in the art. For example, assays measuring proliferation include such assays as chemosensitivity to neutral red dye (Cavanaugh et al., *Investigational New Drugs* 8:347–354, 1990), incorporation of radiolabelled nucleotides (Cook et al., *Analytical Biochem.* 179:1–7, 1989), incorporation of 5-bromo-2'-deoxyuridine (BrdU) in the DNA of proliferating cells (Porstmann et al., *J. Immunol. Methods* 82:169–179, 1985), and use of tetrazolium salts (Mosmann, *J. Immunol. Methods* 65:55–63, 1983; Alley et al., *Cancer Res.* 48:589–601, 1988; Marshall et al., *Growth Reg.* 5:69–84, 1995; and Scudiero et al., *Cancer Res.* 48:4827–4833, 1988). Assays measuring differentiation include, for example, measuring cell-surface markers associated with stage-specific expression of a tissue, enzymatic activity, functional activity or morphological changes (Watt, *FASEB,* 5:281–284, 1991; Francis, *Differentiation* 57:63–75, 1994; Raes, *Adv. Anim. Cell Biol. Technol. Bioprocesses,* 161–71, 1989).

In vivo assays for evaluating the effect of polypeptides such as cystatin T on spermatogenesis are well known in the art. For example, compounds can be injected intraperitoneally for a specific time duration. After the treatment period, animals are sacrificed and testes removed and weighed. Testicles are homogenized and sperm head counts are made (Meistrich et al., *Exp. Cell Res.* 99:72–8, 1976).

Ligand-binding receptor polypeptides can also be used within other assay systems known in the art. Such systems include Scatchard analysis for determination of binding affinity (see Scatchard, *Ann. NY Acad. Sci.* 51: 660–72, 1949) and calorimetric assays (Cunningham et al., *Science* 253:545–8, 1991; Cunningham et al., *Science* 245:821–5, 1991).

The invention also provides use of cystatin T polypeptides and polynucleotides in diagnostic applications. Cystatin T polypeptides or polynucleotides can be used, for example, in assays such as for determining circulating levels of polypeptides in a biological sample; or detecting or quantitating soluble polypeptides as marker of underlying pathology or disease. Methods for immunochemical detection of such proteins are known, see for example Esnard et al., (*FEBS Lett.,* 1992). Such biological samples include blood, seminal, testis or interstitial fluids. Cystatin T concentrations can be compared to known cystatins such as cystatin C or to other testicular proteins such as CRES.

The invention also provides anti-cystatin T antibodies. Antibodies to cystatin T can be obtained, for example, using as an antigen the product of a cystatin T expression vector, or cystatin T isolated from a natural source. Particularly useful anti-cystatin T antibodies "bind specifically" with cystatin T. Antibodies are considered to be specifically binding if the antibodies bind to a cystatin T polypeptide, peptide or epitope with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, *Ann. NY Acad. Sci.* 51:660, 1949). Suitable antibodies include antibodies that bind with cystatin T in particular domains.

Anti-cystatin T antibodies can be produced using antigenic cystatin T epitope-bearing peptides and polypeptides. Antigenic epitope-bearing peptides and polypeptides of the present invention contain a sequence of at least nine, preferably between 15 to about 30 amino acids contained within SEQ ID NO:2. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that bind with cystatin T. It is desirable that the amino acid sequence of the epitope-bearing peptide is selected to provide substantial solubility in aqueous solvents (i.e., the sequence includes relatively hydrophilic residues, while hydrophobic residues are preferably avoided). Moreover, amino acid sequences containing proline residues may be also be desirable for antibody production.

Polyclonal antibodies to recombinant cystatin T protein or to cystatin T isolated from natural sources can be prepared using methods well-known to those of skill in the art. See, for example, Green et al., "Production of Polyclonal Antisera," in *Immunochemical Protocols* (Manson, ed.), pages 1–5 (Humana Press 1992), and Williams et al., "Expression of foreign proteins in *E. coli* using plasmid vectors and purification of specific polyclonal antibodies," in *DNA Cloning* 2: Expression Systems, 2nd Edition, Glover et al. (eds.), page 15 (Oxford University Press 1995). The immunogenicity of a cystatin T polypeptide can be increased through the use of an adjuvant, such as alum (aluminum hydroxide) or Freund's complete or incomplete adjuvant. Polypeptides useful for immunization also include fusion polypeptides, such as fusions of cystatin T or a portion thereof with an immunoglobulin polypeptide or with maltose binding protein. The polypeptide immunogen may be a full-length molecule or a portion thereof. If the polypeptide portion is "hapten-like," such portion may be advantageously joined or linked to a macromolecular carrier (such as keyhole limpet hemocyanin (KLH), bovine serum albumin (BSA) or tetanus toxoid) for immunization.

Although polyclonal antibodies are typically raised in animals such as horses, cows, dogs, chicken, rats, mice, rabbits, hamsters, guinea pigs, goats, or sheep, an anti-cystatin T antibody of the present invention may also be derived from a subhuman primate antibody. General techniques for raising diagnostically and therapeutically useful antibodies in baboons may be found, for example, in Goldenberg et al., international patent publication No. WO 91/11465, and in Losman et al., *Int. J. Cancer* 46:310, 1990. Antibodies can also be raised in transgenic animals such as transgenic sheep, cows, goats or pigs, and can also be expressed in yeast and fungi in modified forms as will as in mammalian and insect cells.

Alternatively, monoclonal anti-cystatin T antibodies can be generated. Rodent monoclonal antibodies to specific antigens may be obtained by methods known to those skilled in the art (see, for example, Kohler et al., *Nature* 256:495 (1975), Coligan et al. (eds.), *Current Protocols in Immunology,* Vol. 1, pages 2.5.1–2.6.7 (John Wiley & Sons 1991), Picksley et al., "Production of monoclonal antibodies against proteins expressed in *E. coli,*" in *DNA Cloning* 2: *Expression Systems, 2nd Edition, Glover et al. (eds.),* page 93 (Oxford University Press 1995)).

Briefly, monoclonal antibodies can be obtained by injecting mice with a composition comprising a cystatin T gene product, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

In addition, an anti-cystatin T antibody of the present invention may be derived from a human monoclonal antibody. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13, 1994, Lonberg et al., Nature 368:856, 1994, and Taylor et al., *Int. Immun.* 6:579, 1994.

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1–2.7.12 and pages 2.9.1–2.9.3; Baines et al., "Purification of Immunoglobulin G (IgG)," in *Methods in Molecular Biology*, Vol. 10, pages 79–104 (The Humana Press, Inc. 1992)).

For particular uses, it may be desirable to prepare fragments of anti-cystatin T antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., *Arch Biochem. Biophys.* 89:230, 1960, Porter, *Biochem. J.* 73:119, 1959, Edelman et al., in *Methods in Enzymology* Vol. 1, page 422 (Academic Press 1967), and by Coligan, ibid.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., *Proc. Natl. Acad. Sci. USA* 69:2659, 1972. Alternatively, the variable chains can be linked by an intermolecular disulfide bond or cross-linked by chemicals such as gluteraldehyde (see, for example, Sandhu, *Crit. Rev. Biotech.* 12:437, 1992).

The Fv fragments may comprise $V_H$ and $V_L$ chains which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing scFvs are described, for example, by Whitlow et al., *Methods: A Companion to Methods in Enzymology* 2:97, 1991, also see, Bird et al., *Science* 242:423, 1988, Ladner et al., U.S. Pat. No. 4,946,778, Pack et al., *Bio/Technology* 11:1271, 1993, and Sandhu, supra.

As an illustration, a scFV can be obtained by exposing lymphocytes to cystatin T polypeptide in vitro, and selecting antibody display libraries in phage or similar vectors (for instance, through use of immobilized or labeled cystatin T protein or peptide). Genes encoding polypeptides having potential cystatin T polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409, Ladner et al., U.S. Pat. No. 4,946,778, Ladner et al., U.S. Pat. No. 5,403,484, Ladner et al., U.S. Pat. No. 5,571,698, and Kay et al., *Phage Display of Peptides and Proteins* (Academic Press, Inc. 1996)) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the cystatin T sequences disclosed herein to identify proteins which bind to cystatin T.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106, 1991), Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995), and Ward et al., "Genetic Manipulation and Expression of Antibodies," in *Monoclonal Antibodies: Principles and Applications*, Birch et al., (eds.), page 137 (Wiley-Liss, Inc. 1995)).

Alternatively, an anti-cystatin T antibody may be derived from a "humanized" monoclonal antibody. Humanized monoclonal antibodies are produced by transferring mouse complementary determining regions from heavy and light variable chains of the mouse immunoglobulin into a human variable domain. Typical residues of human antibodies are then substituted in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat. Acad. Sci. USA* 86:3833, 1989. Techniques for producing humanized monoclonal antibodies are described, for example, by Jones et al., *Nature* 321:522, 1986, Carter et al., *Proc. Nat. Acad. Sci. USA* 89:4285, 1992, Sandhu, *Crit. Rev. Biotech.* 12:437, 1992, Singer et al., *J. Immun.* 150:2844, 1993, Sudhir (ed.), *Antibody Engineering Protocols* (Humana Press, Inc. 1995), Kelley, "Engineering Therapeutic Antibodies," in *Protein Engineering: Principles* and *Practice,* Cleland et al. (eds.), pages 399–434 (John Wiley & Sons, Inc. 1996), and by Queen et al., U.S. Pat. No. 5,693,762 (1997).

Polyclonal anti-idiotype antibodies can be prepared by immunizing animals with anti-cystatin T antibodies or antibody fragments, using standard techniques. See, for example, Green et al., "Production of Polyclonal Antisera," in *Methods In Molecular Biology: Immunochemical Protocols,* Manson (ed.), pages 1–12 (Humana Press 1992). Also, see Coligan, ibid. at pages 2.4.1–2.4.7. Alternatively, monoclonal anti-idiotype antibodies can be prepared using anti-cystatin T antibodies or antibody fragments as immunogens with the techniques, described above. As another alternative, humanized anti-idiotype antibodies or subhuman primate anti-idiotype antibodies can be prepared using the above-described techniques. Methods for producing anti-idiotype antibodies are described, for example, by Irie, U.S. Pat. No. 5,208,146, Greene, et. al., U.S. Pat. No. 5,637,677, and Varthakavi and Minocha, *J. Gen. Virol.* 77:1875, 1996.

Genes encoding polypeptides having potential cystatin T polypeptide binding domains, "binding proteins", can be obtained by screening random or directed peptide libraries displayed on phage (phage display) or on bacteria, such as *E. coli.* Nucleotide sequences encoding the polypeptides can be obtained in a number of ways, such as through random mutagenesis and random polynucleotide synthesis. Alternatively, constrained phage display libraries can also be produced. These peptide display libraries can be used to screen for peptides which interact with a known target which can be a protein or polypeptide, such as a ligand or receptor, a biological or synthetic macromolecule, or organic or inorganic substances. Techniques for creating and screening such peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Peptide display libraries can be screened using the cystatin T sequences disclosed herein to identify proteins which bind to cystatin T. These "binding proteins" which interact with cystatin T polypeptides can be used essentially like an antibody.

A variety of assays known to those skilled in the art can be utilized to detect antibodies and/or binding proteins which specifically bind to cystatin T proteins or peptides. Exemplary assays are described in detail in *Antibodies: A Laboratory Manual,* Harlow and Lane (Eds.), Cold Spring Harbor Laboratory Press, 1988. Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay. In addition, antibodies can be screened for binding to wild-type versus mutant cystatin T protein or polypeptide.

Antibodies and binding proteins to cystatin T may be used for tagging cells that express cystatin T; for isolating cystatin T by affinity purification; for diagnostic assays for determining circulating levels of cystatin T polypeptides; for detecting or quantitating soluble cystatin T as marker of underlying pathology or disease; in analytical methods employing FACS; for screening expression libraries; for generating anti-idiotypic antibodies; and as neutralizing antibodies or as antagonists to block cystatin T polypeptide modulation of spermatogenesis or like activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Moreover, antibodies to cystatin T or fragments thereof may be used in vitro to detect denatured cystatin T or fragments thereof in assays, for example, Western Blots or other assays known in the art.

Antibodies or polypeptides herein can also be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (receptor or antigen, respectively, for instance). More specifically, cystatin T polypeptides or anti-cystatin T antibodies, or bioactive fragments or portions thereof, can be coupled to detectable or cytotoxic molecules and delivered to a mammal having cells, tissues or organs that express the anti-complementary molecule.

Molecules of the present invention can be used to identify and isolate cysteine proteinases with which cystatin T polypeptide interacts. For example, proteins and peptides of the present invention can be immobilized on a column and membrane preparations run over the column (*Immobilized Affinity Ligand Techniques,* Hermanson et al., eds., Academic Press, San Diego, Calif., 1992, pp.195–202). Proteins and peptides can also be radiolabeled (*Methods in Enzymol.,* vol. 182, "Guide to Protein Purification", M. Deutscher, ed., Acad. Press, San Diego, 1990, 721–37) or photoaffinity labeled (Brunner et al., *Ann. Rev. Biochem.* 62:483–514, 1993 and Fedan et al., *Biochem. Pharmacol.* 33:1167–80, 1984) and specific cysteine proteinases can be identified.

Assays known in the art for evaluating cysteine protease inhibition may be employed to identify or evaluate cystatin T polypeptide agonists, antagonists, homologs, paralogs, and the like. Such assays include those described by Sotiropoulou et al., *J. Biol. Chem.* 272: 903–10, 1997 (papain assay); Adenis et al., *Cancer Letters* 96: 267–75, 1995 (cathepsin B, L and D activity assays); Hall et al., *Biochem. J.* 291: 123–9, 1993 (enzyme inhibition assays); Laszlo et al., *Acta Paediatrica Hungarica* 28: 175–78, 1987 (activity of cathepsins B, H and L in the serum of cystic fibrosis patients); Luthgens et al., *Cancer Detection and Prevention* 17: 387–97, 1993 (bronchoalveolar lavage methods); Luisetti et al., *Respiration* 59: 24–7, 1992 (bronchoalveolar lavage evaluation of protease-anti-protease imbalance); and the like.

Assays known in the art for evaluating urokinase-type plasminogen activator (uPA) may also be used to identify or evaluate cystatin T polypeptide agonists, antagonists, homologs, paralogs, and the like. Such assays include those described by Silberman et al., *J. Biol. Chem.* 272: 5927–35, 1997 (Northern analysis); Nauland & Rijken, *Eur. J. Biochem.* 223: 497–501, 1994 (two chain uPA activity); Schmitt et al., *Biol. Chem.* 373: 611–22, 1992 (quantitative assessment of uPA and proteolytic factors in tumor tissue extracts); Kobayashi et al., *J. Biol. Chem.* 266: 5147–52, 1991 (assays for enzymatic activity and Pro-uPA-cathepsin B or D interaction); and the like.

An additional aspect of the present invention provides methods for identifying agonists or antagonists of the cystatin T polypeptides disclosed above, which agonists or antagonists may have valuable therapeutic properties as discussed further herein. Within one embodiment, there is provided a method of identifying cystatin T polypeptide agonists, comprising providing cells responsive to a cystatin T polypeptide, culturing the cells in the presence of a test compound and comparing the cellular response with the cell cultured in the presence of the cystatin T polypeptide, and selecting the test compounds for which the cellular response is of the same type. Alternatively, putative agonists of cystatin T polypeptide can be evaluated as generally described above using cysteine proteinase binding assays. If the putative agonist binds cysteine proteinases, such as the plant proteinase papain, with an affinity within an order of magnitude below the cystatin T polypeptide or higher, that putative agonist is selected as an agonist.

Within another embodiment, there is provided a method of identifying antagonists of cystatin T polypeptide, comprising providing cells responsive to a cystatin T polypeptide, culturing a first portion of the cells in the presence of cystatin T polypeptide, culturing a second portion of the cells in the presence of the cystatin T polypeptide and a test compound, and detecting a decrease in a cellular response of the second portion of the cells as compared to the first portion of the cells. Alternatively, putative antagonists of cystatin T polypeptide can be evaluated as generally described above using cysteine proteinase binding assays. If the putative antagonist inhibits cystatin T polypeptide binding to cysteine proteinases, such as the plant proteinase papain, by at least one order of magnitude, that putative antagonist is selected as an antagonist.

Cystatin T polypeptide agonists are useful in applications requiring modulation of spermatogenesis, such as in in vitro or in vivo study of sperm development and maturation. Cystatin T polypeptide antagonists are useful in applications requiring inhibition of spermatogenesis, such as in in vitro or in vivo study of fertilization and conception.

Polynucleotides encoding cystatin T polypeptides are useful within gene therapy applications where it is desired to increase or inhibit cystatin T activity. If a mammal has a mutated or absent cystatin T gene, the cystatin T gene can be introduced into the cells of the mammal. In one embodiment, a gene encoding a cystatin T polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–8, 1989).

In another embodiment, a cystatin T gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Patent Publication NO: WO 95/07358, published Mar. 16, 1995 by Dougherty et al.; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–7, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–7, 1992; Wu et al., *J. Biol. Chem.* 263:14621–4, 1988.

Antisense methodology can be used to inhibit cystatin T gene transcription, such as to inhibit cell proliferation in vivo. Polynucleotides that are complementary to a segment of a cystatin T-encoding polynucleotide (e.g., a polynucleotide as set froth in SEQ ID NO:1) are designed to bind to cystatin T-encoding mRNA and to inhibit translation of such mRNA. Such antisense polynucleotides are used to inhibit expression of cystatin T polypeptide-encoding genes in cell culture or in a subject.

Transgenic mice, engineered to express the cystatin T gene, and mice that exhibit a complete absence of cystatin T gene function, referred to as "knockout mice" (Snouwaert et al., *Science* 257:1083, 1992), may also be generated (Lowell et al., *Nature* 366:740–2, 1993). These mice may be employed to study the cystatin T gene and the protein encoded thereby in an in vivo system.

For pharmaceutical use, the proteins of the present invention are formulated for parenteral, such as intravenous or subcutaneous, delivery according to conventional methods. Other modes of administration include tablets, caplets, pills, powders, granules, eyedrops, oral or ocular solutions or suspensions, ocular ointments, transdermal patches and oil-in-water emulsions. Intravenous administration will be by bolus injection or infusion over a typical period of one to several hours. In general, pharmaceutical formulations will include a cystatin T protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy,* Gennaro, ed., Mack Publishing Co., Easton, Pa., 19th ed., 1995.

As used herein a "pharmaceutically effective amount" of a cystatin T polypeptide, agonist or antagonist is an amount sufficient to induce a desired biological result. The result can be alleviation of the signs, symptoms, or causes of a disease, or any other desired alteration of a biological system. For example, an effective amount of a cystatin T polypeptide is that which provides either subjective relief of symptoms or an objectively identifiable improvement as noted by the clinician or other qualified observer. Effective amounts of the cystatin T polypeptides can vary widely depending on the disease or symptom to be treated. The amount of the polypeptide to be administered and its concentration in the formulations, depends upon the vehicle selected, route of administration, the potency of the particular polypeptide, the clinical condition of the patient, the side effects and the stability of the compound in the formulation. Thus, the clinician will employ the appropriate preparation containing the appropriate concentration in the formulation, as well as the amount of formulation administered, depending upon clinical experience with the patient in question or with similar patients. Such amounts will depend, in part, on the particular condition to be treated, age, weight, and general health of the patient, and other factors evident to those skilled in the art. Doses for specific compounds may be determined from in vitro or ex vivo studies in combination with studies on experimental animals.

The dosages of the present compounds used to practice the invention include dosages effective to result in the desired effects. Estimation of appropriate dosages effective for the individual patient is well within the skill of the ordinary prescribing physician or other appropriate health care practitioner. As a guide, the clinician can use conventionally available advice from a source such as the Physician's Desk Reference, 48$^{th}$ Edition, Medical Economics Data Production Co., Montvale, N.J. 07645–1742 (1994).

The present invention, thus generally described, will be understood more readily by reference to the following example, which is provided by way of illustration and is not intended to be limiting of the present invention.

EXAMPLES

Example 1

Identification of the Cystatin T Sequence

The novel cystatin T polypeptide-encoding polynucleotides of the present invention were initially identified by querying an EST database for cystatin homologs. An EST discovered and predicted to be related to the cystatin family, but lacked the 5' half the polynucleotide sequence. Oligonucleotides ZC17516 (SEQ ID NO:21) and ZC17517 (SEQ ID NO:22) derived from the EST sequence were used as primers to amplify the region from a variety of cDNA libraries. Amplification of the sequence occurred only when using testis libraries. To identify the corresponding full length cDNA, 5' RACE was used to obtain the missing sequence. Murine testis cDNA was used as a template and oligonucleotides ZC18696 (SEQ ID NO:16) and ZC18369 (SEQ ID NO:17) were used a primers. The sequence of the cloned PCR produce was confirmed by sequence analysis. Using an Invitrogen S.N.A.P.™ Miniprep kit (Invitrogen, Corp., San Diego, Calif.) according to manufacturer's instructions a 5 ml overnight culture in LB+50 µg/ml ampicillin was prepared. The template was sequenced on an ABIPRISM™ model 377 DNA sequencer (Perkin-Elmer Cetus, Norwalk, Conn.) using the ABI PRISM™ Dye Terminator Cycle Sequencing Ready Reaction Kit (Perkin-Elmer Corp.) according to manufacturer's instructions. Sequencing reactions were carried out in a Hybaid Omni-Gene Temperature Cycling System (National Labnet Co., Woodbridge, N.Y.). SEQUENCHER™ 3.0 sequence analysis software (Gene Codes Corporation, Ann Arbor, Mich.) was used for data analysis. The resulting 490 bp sequence murine cystatin T sequence is disclosed in SEQ ID NO:1.

Example 2

Tissue Distribution

Mouse Multiple Tissue Northern Blot (Clontech) was probed to determine the murine tissue distribution of murine cystatin T expression. An 188 bp DNA probe derived from the clone described above that contains the 3' end of the cystatin T polynucleotide sequence (SEQ ID NO:1) including 30 bp 3'UTR was generated by PCR and mouse testis cDNA as a template. The probe was radioactively using a Rediprime II DNA Labeling System (Amersham Pharmacia Biotech, Inc., Piscataway, N.J.) according to the manufacturer's specifications. The probe was purified using a NUC-TRAP push column (Stratagene Cloning Systems, La Jolla, Calif.). ExpressHyb™ (Clontech) solution was used for prehybridization and as a hybridizing solution for the Northern blots. Hybridization took place overnight at 65° C. using $1.0 \times 10^6$ cpm/ml of labeled probe, and the blots were then washed at 4 times at 25° C. in 2×SSC, 0.1% SDS, followed by 2 washes at 50° C. in 0.1×SSC, 0.1% SDS and one wash at 56° C. in 0.1×SSC, 0.1% SDS. A 1.0 kb transcript was detected in testis tissue only.

A mouse multiple tissue sub-blot was prepared by flash freezing mouse bladder, colon, epididymus, prostate, seminal vesicle, testis, was deferens, ovary and uterus tissues in liquid nitrogen. The tissues were then processed using RNeasy® Total RNA System (Qiagen) according to manufacturer's instruction. Twenty milligrams of the total RNA from each tissue sample separated by 1.5% agarose mini gel (Stratagene Cloning Systems, La Jolla, Calif.) electrophoresis in formaldehyde/phosphate buffer. The RNA was blotted overnight onto a nytran filter (Schleicher & Schuell, Keene, N.H.) and the filter was UV crosslinked (1,200 µJoules) in a STRATALINKER® 2400 UV crosslinker (Stratagene Cloning Systems) and then baked at 80° C. for 30 minutes. Hybridization was as described above. Expression was detected in testis only.

A mouse RNA Master Blot™ (Clontech) was probed as described above. Expression was detected only in testis.

A mouse Embryo Northern Blot (Clontech) was also probed to determine expression of cystatin T in embryonic mouse tissue. Northern blot analysis was performed as described above. A 1.0 kb transcript was detected in 7 day old tissue only.

An interspecies Zoo blot (Clontech) was probed as described above. The blots were then washed 4 times at 25° C. in 2×SSC, 0.1% SDS, followed by 3 washes at 50° C. in 0.1×SSC, 0.1% SDS. A single band is present in mouse and rabbit, two bands are present in rat and potentially in human and monkey.

A mouse testis blot was probed as described above. The blot was prepared from TM3, a murine Leydig cell line (ATCC No: CRL-1714), a murine Sertoli cell line TM4 (ATCC No: CRL-1715), two murine Leydig tumor cell lines, MLTC-1 (ATCC No: CRL-2065) and I-10 (ATCC No:CCL-83) and a germ cell line, GC-1 spg (ATCC No:CRL-2053). Total cytoplasmic RNA was isolated essentially as described by Davis et al., Preparation and analysis of RNA from eukaryotic cell. In *Basic Methods in Molecular Biology*, Elsevier Science Publishing Co., Inc. New York, pp 130–5, 1986. Mouse testis and liver tissue were homogenized using the TH115 Tissue Homogenizer (Omni International, Warrenton, Va.). Total RNA was isolated using the RNeasy® Total RNA System (Qiagen) according to manufacturer's instruction. Twenty milligrams of the total RNA from each tissue sample separated by 1% agarose mini gel (Stratagene Cloning Systems, La Jolla, Calif.) electrophoresis in formaldehyde/phosphate buffer. The RNA was blotted overnight onto a GeneScreen membrane (NEN, Boston, Mass.) and the filter was UV crosslinked (1,200 μJoules) in a STRATALINKER® 2400 UV crosslinker (Stratagene Cloning Systems) and then baked at 80° C. for 30 minutes. Hybridization was as described above. Expression was detected in testis only.

Rat organ blots were generated using brain, heart, kidney, liver, lung, pancreas, skeletal muscle, spleen and testis tissue from Sprague Dawley rats (67 days old) and epididymis, prostate, testis, ovary, uterine tissue from 90 day old Sprague Dawley rats. Probing with $^{32}$P labeled full length murine Cystatin T indicated that expression was only in testis.

Example 3

Chromosomal Localization

Murine cystatin T was mapped by PCR using commercially available mouse T31 whole genome radiation hybrid (WGRH) panel (Research Genetics, Inc., Huntsville, Ala.) and Map Manager QT linkage analysis program. The T 31 WGRH panel contains DNA from each of 100 radiation hybrid clones, plus two control DNAs (the 129aa donor and the A23 recipient). For the mapping of murine cystatin T with the T31 WGRH panel, 20 μl reactions were set up in 96-well microtiter plates (Stratagene Cloning Systems, La Jolla, Calif.) and used in RoboCycler Gradient 96 thermal cyclers (Strategen). Each of the 102 PCR reactions consisted of 2 μl 10×KlenTaq PCR reaction buffer (Clontech, Palo Alto, Calif.), 1.6 μl dNTPs mix (2.5 mM each, Perkin-Elmer Cetus, Norwalk, Conn.), 1 μl sense primer ZC 20814 (SEQ ID NO:19), 1 μl antisense primer ZC20815 (SEQ ID NO:20), 2 μl RediLoad (Research Genetics, Inc.), 0.4 μl 50×Advantage KlenTaq Polymerase Mix (Clontech), 25 ng of DNA from an individual hybrid clone or control and ddH$_2$O for a total volume of 20 μl. The PCR cycle conditions were as follows: 5 minutes at 94° C. (1 cycle), followed by 45 seconds at 94° C., 45 seconds at 62° C. and 1 minute and 15 seconds at 72° C. (35 cycles) followed by a final extension of 7 minutes at 72° C. The reactions were separated by electrophoresis on a 2% agarose gel (Life Technologies, Gaithersburg, Md.).

At P=0.0001, murine zcys3 linked to the marker D2Mit194 with a LOD score of 9.07. D2Mit194 has been mapped at 81.4 cM on mouse chromosome 2. This is a known region of synteny or linkage conservation with the 20p11.2 region of human chromosome 20, where a cystatin gene cluster has been mapped containing CST1–5 and 2 pseudogenes.

Example 4

Stage Specific Northern Analysis

To determine if the gene encoding murine Cystatin T is regulated during the cycle of the seminiferous epithelium, stage synchronized testes were obtained from adult Sprague-Dawley rats as described by Wright et al. (*Biology of Reproduction* 29:257–70, 1983). Seminiferous tubule fragments corresponding to the following stages, I, II–III, IV–V, VI, VIIab, VIIcd, VIII, IX–XI, XII, XIII–XIV, in the cycle of the seminiferous epithelium were used. The isolated tubule fragments were solublized in TriZol (Life Technologies) and total RNA was isolated according to manufacturer's instructions. The total RNA was quantitated and 7.5 μg of total RNA from each stage was fractionated using a 1.2% agarose gel in 1% formaldehyde and MOPS buffer, transferred to nylon membrane, and cross-linked. The blots were probed with $^{32}$P labeled, full length murine Cystatin T DNA as described above. The probe was heat denatured and added to prehybridization solution for overnight hybridization. Blots were washed at room temperature, 2×SSC/0.1% SDS for 10 minutes, the 65° C. 0.2% SSC/0.1% SDS, twice for 15 minutes, then exposed to film. As a loading control, the blots were probed with $^{32}$P-labeled CHO B, also known as ribosomal protein S2 (Tohgo et al., *FEBS Lett.* 340:133–8, 1994).

The results of the Northern Blot analysis indicate that the murine Cystatin T gene is regulated during the cycle of the seminiferous epithelium. Table 5 shows the amount of the Cystatin T gene relative to CHO B at the various stages tested.

TABLE 5

| Fragment | Cystatin T/CHO B |
|---|---|
| I | 0.04 |
| II–III | 0.00 |
| IV–V | 0.0 |
| VI | 0.01 |
| VIIab | 0.252 |
| VIIcd | 0.670 |
| VIII | 1.0 |
| IX–XI | 0.954 |
| IX–XIII | 0.825 |
| XIV | 0.0 |

The gene encoding murine Cystatin T is highly regulated during the cycle of the seminiferous epithelium. It is very low or undetectable during stages XIV–VI and rises dramatically during stages VIIab and XII, then decreased abruptly.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polynucleotide encoding a polypeptide comprising 10 or more contiguous amino acid residues of SEQ ID NO: 2, wherein said polypeptide comprises SEQ ID NO: 14 and inhibits cysteine proteinase.

2. An isolated polynucleotide according to claim 1, wherein said polypeptide comprises SEQ ID NO:13.

3. An isolated polynucleotide according to claim 1, wherein said polypeptide comprises amino acid residues 76–138 of SEQ ID NO:2.

4. An isolated polynucleotide that encodes a polypeptide which inhibits cysteine proteinases and hybridizes under stringent conditions to SEQ ID NO: 1, wherein said stringent hybridization conditions comprise hybridizing in 6×SSC at about 65° C. and washing in 0.1×SSC at about 65° C.

5. An isolated polynucleotide molecule consisting of nucleotides 271–459 of SEQ ID NO:1.

6. An isolated polynucleotide that encodes a polypeptide which inhibits cysteine proteinases, wherein said polynucleotide comprises the nucleotide sequence of nucleotides 46 to 468 of SEQ ID NO:1.

7. An isolated polynucleotide according to claim 1, further comprising a DNA segment encoding an affinity tag or binding domain.

8. A polynucleotide encoding a fusion protein comprising a secretory signal sequence having the amino acid sequence of amino acid residues 1–20 of SEQ ID NO:2, wherein said secretory signal sequence is fused to the N-terminus of a polypeptide.

9. A polynucleotide molecule encoding a fusion protein consisting of a first portion and a second portion joined by a peptide bond, said first portion comprising a polypeptide having 10 or more contiguous amino acid residues of SEQ ID NO: 2, wherein said polypeptide comprises SEQ ID NO: 14 and inhibits cysteine proteinases; and said second portion comprising another polypeptide.

10. An expression vector comprising the following operably linked elements: a transcription promoter; a DNA segment encoding a polypeptide comprising 10 or more contiguous amino acid residues of SEQ ID NO: 2, wherein said polypeptide comprises SEQ ID NO: 14 and inhibits cysteine proteinases; and a transcription terminator.

11. An expression vector according to claim 10 further comprising a DNA segment encoding a secretory signal sequence fused to the N-terminus of said polypeptide encoded by said DNA segment.

12. An expression vector according to claim 10, wherein said DNA segment encodes a polypeptide covalently linked amino terminally or carboxy terminally to an affinity tag.

13. A cultured cell into which has been introduced an expression vector according the claim 10, wherein said cultured cell expresses said polypeptide encoded by said DNA segment.

14. A method of producing a polypeptide comprising:
   culturing a cell into which has been introduced an expression vector according to claim 10;
   whereby said cell expresses said polypeptide encoded by said DNA segment; and
   recovering said expressed polypeptide.

* * * * *

SEQUENCE LISTING

<160> NUMBER OF SEQ ID NOS: 22

<210> SEQ ID NO 1
<211> LENGTH: 490
<212> TYPE: DNA
<213> ORGANISM: Mus musculus
<220> FEATURE:
<221> NAME/KEY: CDS
<222> LOCATION: (46)...(468)

<400> SEQUENCE: 1

```
gaaagaaaat aggaacttgg tatgttcctt gaatgaagaa gcacc atg gcc aga ttc      57
                                                 Met Ala Arg Phe
                                                   1 tta cag acc ctg ctg ttc ctg gtg atc acg gtg gag ttt gta tct aga       105
Leu Gln Thr Leu Leu Phe Leu Val Ile Thr Val Glu Phe Val Ser Arg
  5              10                  15                  20 aga gtc gaa gcc tgg ggc tcc cca cag att gtg agg cca ttc gaa gac       153
Arg Val Glu Ala Trp Gly Ser Pro Gln Ile Val Arg Pro Phe Glu Asp
             25                  30                  35 atc ccc aaa tcc tat gtc tat gtg cag cat gca ctc tgg tat gcc atg       201
Ile Pro Lys Ser Tyr Val Tyr Val Gln His Ala Leu Trp Tyr Ala Met
         40                  45                  50 aaa gaa tat aac aag gcc agc aat gac ctc tac aac ttc agg gtg gtg       249
Lys Glu Tyr Asn Lys Ala Ser Asn Asp Leu Tyr Asn Phe Arg Val Val
     55                  60                  65 gat atc cta aaa tct cag gag cag atc aca gac agt ctg gag tat tat       297
Asp Ile Leu Lys Ser Gln Glu Gln Ile Thr Asp Ser Leu Glu Tyr Tyr
 70                  75                  80 ctt gaa gta aac att gcc cga aca atg tgc aag aag att gca gga gat       345
Leu Glu Val Asn Ile Ala Arg Thr Met Cys Lys Lys Ile Ala Gly Asp
 85                  90                  95                 100 aat gaa aac tgc ttg ttt caa cag gat cct aaa atg aaa aag atg gtg       393
Asn Glu Asn Cys Leu Phe Gln Gln Asp Pro Lys Met Lys Lys Met Val
                 105                 110                 115 ttt tgc att ttt att gtt agc tcc aaa cca tgg aag ttt gaa ctt aaa       441
Phe Cys Ile Phe Ile Val Ser Ser Lys Pro Trp Lys Phe Glu Leu Lys
                 120                 125                 130 atg ctg aag aag caa tgc aaa gat atc taatcagcat tcgggacacc            488
Met Leu Lys Lys Gln Cys Lys Asp Ile
             135                 140 tt                                                                    490
```

<210> SEQ ID NO 2
<211> LENGTH: 141
<212> TYPE: PRT
<213> ORGANISM: Homo sapiens

<400> SEQUENCE: 2

```
Met Ala Arg Phe Leu Gln Thr Leu Leu Phe Leu Val Ile Thr Val Glu
  1               5                  10                  15

Phe Val Ser Arg Arg Val Glu Ala Trp Gly Ser Pro Gln Ile Val Arg
                 20                  25                  30

Pro Phe Glu Asp Ile Pro Lys Ser Tyr Val Tyr Val Gln His Ala Leu
             35                  40                  45

Trp Tyr Ala Met Lys Glu Tyr Asn Lys Ala Ser Asn Asp Leu Tyr Asn
         50                  55                  60

Phe Arg Val Val Asp Ile Leu Lys Ser Gln Glu Gln Ile Thr Asp Ser
 65                  70                  75                  80
```

-continued

```
Leu Glu Tyr Tyr Leu Glu Val Asn Ile Ala Arg Thr Met Cys Lys Lys
             85                  90                  95

Ile Ala Gly Asp Asn Glu Asn Cys Leu Phe Gln Gln Asp Pro Lys Met
            100                 105                 110

Lys Lys Met Val Phe Cys Ile Phe Ile Val Ser Ser Lys Pro Trp Lys
        115                 120                 125

Phe Glu Leu Lys Met Leu Lys Lys Gln Cys Lys Asp Ile
        130                 135                 140
```

<210> SEQ ID NO 3
<211> LENGTH: 142
<212> TYPE: PRT
<213> ORGANISM: Mus musculus

<400> SEQUENCE: 3

```
Met Ala Lys Pro Leu Trp Leu Ser Leu Ile Leu Phe Ile Ile Pro Val
1               5                   10                  15

Ala Leu Ala Val Gly Val Asp Gln Ser Lys Asn Glu Val Lys Ala Gln
            20                  25                  30

Asn Tyr Phe Gly Ser Ile Asn Ile Ser Asn Ala Asn Val Lys Gln Cys
        35                  40                  45

Val Trp Phe Ala Met Lys Glu Tyr Asn Lys Glu Ser Glu Asp Lys Tyr
    50                  55                  60

Val Phe Leu Val Asp Lys Ile Leu His Ala Lys Leu Gln Ile Thr Asp
65                  70                  75                  80

Arg Met Glu Tyr Gln Ile Asp Val Gln Ile Ser Arg Ser Asn Cys Lys
                85                  90                  95

Lys Pro Leu Asn Asn Thr Glu Asn Cys Ile Pro Gln Lys Lys Pro Glu
            100                 105                 110

Leu Glu Lys Lys Met Ser Cys Ser Phe Leu Val Gly Ala Leu Pro Trp
        115                 120                 125

Asn Gly Glu Phe Asn Leu Leu Ser Lys Glu Cys Lys Asp Val
    130                 135                 140
```

<210> SEQ ID NO 4
<211> LENGTH: 142
<212> TYPE: PRT
<213> ORGANISM: Homo sapiens

<400> SEQUENCE: 4

```
Met Pro Arg Cys Arg Trp Leu Ser Leu Ile Leu Thr Ile Pro Leu
1               5                   10                  15

Ala Leu Val Ala Arg Lys Asp Pro Lys Lys Asn Glu Thr Gly Val Leu
            20                  25                  30

Arg Lys Leu Lys Pro Val Asn Ala Ser Asn Ala Asn Val Lys Gln Cys
        35                  40                  45

Leu Trp Phe Ala Met Gln Glu Tyr Asn Lys Glu Ser Glu Asp Lys Tyr
    50                  55                  60

Val Phe Leu Val Val Lys Thr Leu Gln Ala Gln Leu Gln Val Thr Asn
65                  70                  75                  80

Leu Leu Glu Tyr Leu Ile Asp Val Glu Ile Ala Arg Ser Asp Cys Arg
                85                  90                  95

Lys Pro Leu Ser Thr Asn Glu Ile Cys Ala Ile Gln Glu Asn Ser Lys
            100                 105                 110

Leu Lys Arg Lys Leu Ser Cys Ser Phe Leu Val Gly Ala Leu Pro Trp
        115                 120                 125
```

```
Asn Gly Glu Phe Thr Val Met Glu Lys Lys Cys Glu Asp Ala
        130                 135                 140
```

<210> SEQ ID NO 5
<211> LENGTH: 140
<212> TYPE: PRT
<213> ORGANISM: Mus musculus

<400> SEQUENCE: 5

```
Met Ala Ser Pro Leu Arg Ser Leu Leu Phe Leu Leu Ala Val Leu Gly
 1               5                  10                  15

Val Ala Trp Ala Ala Thr Pro Lys Gln Gly Pro Arg Met Leu Gly Ala
            20                  25                  30

Pro Glu Glu Ala Asp Ala Asn Glu Glu Gly Val Arg Arg Ala Leu Asp
        35                  40                  45

Phe Ala Val Ser Glu Tyr Asn Lys Gly Ser Asn Asp Ala Tyr His Ser
    50                  55                  60

Arg Ala Ile Gln Val Val Arg Ala Arg Lys Gln Leu Val Ala Gly Val
65                  70                  75                  80

Asn Tyr Phe Phe Asp Val Glu Met Gly Arg Thr Thr Cys Thr Lys Ser
                85                  90                  95

Gln Thr Asn Leu Thr Asp Cys Pro Phe His Asp Gln Pro His Leu Met
            100                 105                 110

Arg Lys Ala Leu Cys Ser Phe Gln Ile Tyr Ser Val Pro Trp Lys Gly
        115                 120                 125

Thr His Ser Leu Thr Lys Phe Ser Cys Lys Asn Ala
    130                 135                 140
```

<210> SEQ ID NO 6
<211> LENGTH: 146
<212> TYPE: PRT
<213> ORGANISM: Homo sapiens

<400> SEQUENCE: 6

```
Met Ala Gly Pro Leu Arg Ala Pro Leu Leu Leu Leu Ala Ile Leu Ala
 1               5                  10                  15

Val Ala Leu Ala Val Ser Pro Ala Ala Gly Ser Ser Pro Gly Lys Pro
            20                  25                  30

Pro Arg Leu Val Gly Gly Pro Met Asp Ala Ser Val Glu Glu Glu Gly
        35                  40                  45

Val Arg Arg Ala Leu Asp Phe Ala Val Gly Glu Tyr Asn Lys Ala Ser
    50                  55                  60

Asn Asp Met Tyr His Ser Arg Ala Leu Gln Val Val Arg Ala Arg Lys
65                  70                  75                  80

Gln Ile Val Ala Gly Val Asn Tyr Phe Leu Asp Val Glu Leu Gly Arg
                85                  90                  95

Thr Thr Cys Thr Lys Thr Gln Pro Asn Leu Asp Asn Cys Pro Phe His
            100                 105                 110

Asp Gln Pro His Leu Lys Arg Lys Ala Phe Cys Ser Phe Gln Ile Tyr
        115                 120                 125

Ala Val Pro Trp Gln Gly Thr Met Thr Leu Ser Lys Ser Thr Cys Gln
    130                 135                 140

Asp Ala
145
```

<210> SEQ ID NO 7

-continued

```
<211> LENGTH: 142
<212> TYPE: PRT
<213> ORGANISM: Homo sapiens

<400> SEQUENCE: 7

Met Met Trp Pro Met His Thr Pro Leu Leu Leu Thr Ala Leu Met
1               5                   10                  15

Val Ala Val Ala Gly Ser Ala Ser Ala Gln Ser Arg Thr Leu Ala Gly
            20                  25                  30

Gly Ile His Ala Thr Asp Leu Asn Asp Lys Ser Val Gln Arg Ala Leu
            35                  40                  45

Asp Phe Ala Ile Ser Glu Tyr Asn Lys Val Ile Asn Lys Asp Glu Tyr
    50                  55                  60

Tyr Ser Arg Pro Leu Gln Val Met Ala Ala Tyr Gln Gln Ile Val Gly
65                  70                  75                  80

Gly Val Asn Tyr Tyr Phe Asn Val Lys Phe Gly Arg Thr Thr Cys Thr
                85                  90                  95

Lys Ser Gln Pro Asn Leu Asp Asn Cys Pro Phe Asn Asp Gln Pro Lys
            100                 105                 110

Leu Lys Glu Glu Glu Phe Cys Ser Phe Gln Ile Asn Glu Val Pro Trp
        115                 120                 125

Glu Asp Lys Ile Ser Ile Leu Asn Tyr Lys Cys Arg Lys Val
    130                 135                 140

<210> SEQ ID NO 8
<211> LENGTH: 149
<212> TYPE: PRT
<213> ORGANISM: Homo sapiens

<400> SEQUENCE: 8

Met Ala Arg Ser Asn Leu Pro Leu Ala Leu Gly Leu Ala Leu Val Ala
1               5                   10                  15

Phe Cys Leu Leu Ala Leu Pro Arg Asp Ala Arg Ala Arg Pro Gln Glu
            20                  25                  30

Arg Met Val Gly Glu Leu Arg Asp Leu Ser Pro Asp Asp Pro Gln Val
            35                  40                  45

Gln Lys Ala Ala Gln Ala Ala Val Ala Ser Tyr Asn Met Gly Ser Asn
    50                  55                  60

Ser Ile Tyr Tyr Phe Arg Asp Thr His Ile Ile Lys Ala Gln Ser Gln
65                  70                  75                  80

Leu Val Ala Gly Ile Lys Tyr Phe Leu Thr Met Glu Met Gly Ser Thr
                85                  90                  95

Asp Cys Arg Lys Thr Arg Val Thr Gly Asp His Val Asp Leu Thr Thr
            100                 105                 110

Cys Pro Leu Ala Ala Gly Ala Gln Gln Glu Lys Leu Arg Cys Asp Phe
        115                 120                 125

Glu Val Leu Val Val Pro Trp Gln Asn Ser Ser Gln Leu Leu Lys His
    130                 135                 140

Asn Cys Val Gln Met
145

<210> SEQ ID NO 9
<211> LENGTH: 145
<212> TYPE: PRT
<213> ORGANISM: Homo sapiens

<400> SEQUENCE: 9
```

Met Arg Ala Ala Gly Thr Leu Leu Ala Phe Cys Cys Leu Val Leu Ser
1               5                   10                  15

Thr Thr Gly Gly Pro Ser Pro Asp Thr Cys Ser Gln Asp Leu Asn Ser
            20                  25                  30

Arg Val Lys Pro Gly Phe Pro Lys Thr Ile Lys Thr Asn Asp Pro Gly
            35                  40                  45

Val Leu Gln Ala Ala Arg Tyr Ser Val Glu Lys Phe Asn Asn Cys Thr
50                  55                  60

Asn Asp Met Phe Leu Phe Lys Glu Ser Arg Ile Thr Arg Ala Leu Val
65                  70                  75                  80

Gln Ile Val Lys Gly Leu Lys Tyr Met Leu Glu Val Glu Ile Gly Arg
                85                  90                  95

Thr Thr Cys Lys Lys Asn Gln His Leu Arg Leu Asp Cys Asp Phe
            100                 105                 110

Gln Thr Asn His Thr Leu Lys Gln Thr Leu Ser Cys Tyr Ser Glu Val
            115                 120                 125

Trp Val Val Pro Trp Leu Gln His Phe Glu Val Pro Val Leu Arg Cys
        130                 135                 140

His
145

<210> SEQ ID NO 10
<211> LENGTH: 149
<212> TYPE: PRT
<213> ORGANISM: Homo sapiens

<400> SEQUENCE: 10

Met Ala Arg Ser Asn Leu Pro Leu Ala Leu Gly Leu Ala Leu Val Ala
1               5                   10                  15

Phe Cys Leu Leu Ala Leu Pro Arg Asp Ala Arg Ala Arg Pro Gln Glu
            20                  25                  30

Arg Met Val Gly Glu Leu Arg Asp Leu Ser Pro Asp Asp Pro Gln Val
            35                  40                  45

Gln Lys Ala Ala Gln Ala Val Ala Ser Tyr Asn Met Gly Ser Asn
50                  55                  60

Ser Ile Tyr Tyr Phe Arg Asp Thr His Ile Ile Lys Ala Gln Ser Gln
65                  70                  75                  80

Leu Val Ala Gly Ile Lys Tyr Phe Leu Thr Met Glu Met Gly Ser Thr
                85                  90                  95

Asp Cys Arg Lys Thr Arg Val Thr Gly Asp His Val Asp Leu Thr Thr
            100                 105                 110

Cys Pro Leu Ala Ala Gly Ala Gln Gln Glu Lys Leu Arg Cys Asp Phe
            115                 120                 125

Glu Val Leu Val Val Pro Trp Gln Asn Ser Ser Gln Leu Leu Lys His
        130                 135                 140

Asn Cys Val Gln Met
145

<210> SEQ ID NO 11
<211> LENGTH: 141
<212> TYPE: PRT
<213> ORGANISM: Homo sapiens

<400> SEQUENCE: 11

Met Ala Arg Pro Leu Cys Thr Leu Leu Leu Leu Met Ala Thr Leu Ala
1               5                   10                  15

```
Gly Ala Leu Ala Ser Ser Ser Lys Glu Glu Asn Arg Ile Ile Pro Gly
             20                  25                  30

Gly Ile Tyr Asp Ala Asp Leu Asn Asp Glu Trp Val Gln Arg Ala Leu
             35                  40                  45

His Phe Ala Ile Ser Glu Tyr Asn Lys Ala Thr Glu Asp Glu Tyr Tyr
 50                  55                  60

Arg Arg Pro Leu Gln Val Leu Arg Ala Arg Glu Gln Thr Phe Gly Gly
 65                  70                  75                  80

Val Asn Tyr Phe Phe Asp Val Glu Val Gly Arg Thr Ile Cys Thr Lys
                 85                  90                  95

Ser Gln Pro Asn Leu Asp Thr Cys Ala Phe His Glu Gln Pro Glu Leu
                100                 105                 110

Gln Lys Lys Gln Leu Cys Ser Phe Glu Ile Tyr Glu Val Pro Trp Glu
            115                 120                 125

Asp Arg Met Ser Leu Val Asn Ser Arg Cys Gln Glu Ala
            130                 135                 140

<210> SEQ ID NO 12
<211> LENGTH: 141
<212> TYPE: PRT
<213> ORGANISM: Homo sapiens

<400> SEQUENCE: 12

Met Ala Gln His Leu Ser Thr Leu Leu Leu Leu Ala Thr Leu Ala
 1               5                  10                  15

Val Ala Leu Ala Trp Ser Pro Lys Glu Glu Asp Arg Ile Ile Pro Gly
             20                  25                  30

Gly Ile Tyr Asn Ala Asp Leu Asn Asp Glu Trp Val Gln Arg Ala Leu
             35                  40                  45

His Phe Ala Ile Ser Glu Tyr Asn Lys Ala Thr Lys Asp Asp Tyr Tyr
 50                  55                  60

Arg Arg Pro Leu Arg Val Leu Arg Ala Arg Gln Gln Thr Val Gly Gly
 65                  70                  75                  80

Val Asn Tyr Phe Phe Asp Val Glu Val Gly Arg Thr Ile Cys Thr Lys
                 85                  90                  95

Ser Gln Pro Asn Leu Asp Thr Cys Ala Phe His Glu Gln Pro Glu Leu
                100                 105                 110

Gln Lys Lys Gln Leu Cys Ser Phe Glu Ile Tyr Glu Val Pro Trp Glu
            115                 120                 125

Asn Arg Arg Ser Leu Val Lys Ser Arg Cys Gln Glu Ser
            130                 135                 140

<210> SEQ ID NO 13
<211> LENGTH: 68
<212> TYPE: PRT
<213> ORGANISM: Artificial Sequence
<220> FEATURE:
<223> OTHER INFORMATION: ZCYS3 motif
<221> NAME/KEY: VARIANT
<222> LOCATION: (2)...(7)
<223> OTHER INFORMATION: Each Xaa is independently any amino acid
      residue
<221> NAME/KEY: VARIANT
<222> LOCATION: (9)...(18)
<223> OTHER INFORMATION: Each Xaa is independently any amino acid
      residue
<221> NAME/KEY: VARIANT
<222> LOCATION: (20)...(20)
<223> OTHER INFORMATION: Xaa is any amino acid residue
<221> NAME/KEY: VARIANT
<222> LOCATION: (22)...(28)
```

-continued

```
<223> OTHER INFORMATION: Each Xaa is independently any amino acid
      residue
<221> NAME/KEY: VARIANT
<222> LOCATION: (29)...(33)
<223> OTHER INFORMATION: Each Xaa is independently any amino acid
      residue or absent
<221> NAME/KEY: VARIANT
<222> LOCATION: (35)...(47)
<223> OTHER INFORMATION: Each Xaa is independently any amino acid
      residue
<221> NAME/KEY: VARIANT
<222> LOCATION: (49)...(55)
<223> OTHER INFORMATION: Each Xaa is independently any amino acid
      residue
<221> NAME/KEY: VARIANT
<222> LOCATION: (58)...(67)
<223> OTHER INFORMATION: Each Xaa is independently any amino acid
      residue

<400> SEQUENCE: 13

Gln Xaa Xaa Xaa Xaa Xaa Xaa Tyr Xaa Xaa Xaa Xaa Xaa Xaa Xaa Xaa
 1               5                  10                  15

Xaa Xaa Cys Xaa Lys Xaa Xaa Xaa Xaa Xaa Xaa Xaa Xaa Xaa Xaa Xaa
            20                  25                  30

Xaa Cys Xaa Xaa Xaa Xaa Xaa Xaa Xaa Xaa Xaa Xaa Xaa Xaa Xaa Cys
        35                  40                  45

Xaa Xaa Xaa Xaa Xaa Xaa Xaa Pro Trp Xaa Xaa Xaa Xaa Xaa Xaa Xaa
    50                  55                  60

Xaa Xaa Xaa Cys
65

<210> SEQ ID NO 14
<211> LENGTH: 46
<212> TYPE: PRT
<213> ORGANISM: Artificial Sequence
<220> FEATURE:
<223> OTHER INFORMATION: Cysteine motif
<221> NAME/KEY: VARIANT
<222> LOCATION: (2)...(9)
<223> OTHER INFORMATION: Each Xaa is independently any amino acid
      residue
<221> NAME/KEY: VARIANT
<222> LOCATION: (10)...(11)
<223> OTHER INFORMATION: Each Xaa is independently any amino acid
      residue or absent
<221> NAME/KEY: VARIANT
<222> LOCATION: (13)...(25)
<223> OTHER INFORMATION: Each Xaa is independently any amino acid
      residue
<221> NAME/KEY: VARIANT
<222> LOCATION: (27)...(45)
<223> OTHER INFORMATION: Each Xaa is independently any amino acid
      residue

<400> SEQUENCE: 14

Cys Xaa Xaa Xaa Xaa Xaa Xaa Xaa Xaa Xaa Xaa Cys Xaa Xaa Xaa Xaa
 1               5                  10                  15

Xaa Xaa Xaa Xaa Xaa Xaa Xaa Xaa Xaa Cys Xaa Xaa Xaa Xaa Xaa Xaa
            20                  25                  30

Xaa Xaa Xaa Xaa Xaa Xaa Xaa Xaa Xaa Xaa Xaa Xaa Cys
        35                  40                  45

<210> SEQ ID NO 15
<211> LENGTH: 423
<212> TYPE: DNA
<213> ORGANISM: Artificial Sequence
<220> FEATURE:
<223> OTHER INFORMATION: Degenerate nucleotide sequence encoding the
      zcys3 polypeptide of SEQ ID NO:2
```

```
<221> NAME/KEY: variation
<222> LOCATION: (1)...(423)
<223> OTHER INFORMATION: Each N is independently any nucleotide

<400> SEQUENCE: 15
atggcnmgnt tyytncarac nytnytntty ytngtnatha cngtngartt ygtnwsnmgn      60
mgngtngarg cntggggnws nccncarath gtnmgnccnt tygargayat hccnaarwsn     120
taygtntayg tncarcaygc nytntggtay gcnatgaarg artayaayaa rgcnwsnaay     180
gayytntaya ayttymgngt ngtngayath ytnaarwsnc argarcarat hacngayswn     240
ytngartayt ayytngargt naayathgcn mgnacnatgt gyaaraaat  hgcnggngay     300 aaygaraayt gyytnttyca rcargayccn aaratgaara aratggtntt ytgyathtty     360
athgtnwsnw snaarccntg gaarttygar ytnaaratgy tnaaraarca rtgyaargay     420 ath                                                                  423

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide ZC18696

<400> SEQUENCE: 16
ctacattgac accagctctg                                                 20

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide ZC18369

<400> SEQUENCE: 17
aaggtgtccc gaatgctgat                                                 20

<210> SEQ ID NO 18
<211> LENGTH: 137
<212> TYPE: PRT
<213> ORGANISM: Mus musculus

<400> SEQUENCE: 18

Met Ser Cys Pro Leu Arg Lys Ala Leu Pro Leu Thr Met Leu Leu
 1               5                  10                  15

Leu Leu Leu Ser Phe His Val Leu Ile Thr Pro Val Ser Lys Ala Asn
                20                  25                  30

Lys Glu Thr Asn Arg Ser Val His Phe Ile Pro Thr Val Glu Phe Ala
            35                  40                  45

Val Asn Thr Phe Asn Gln Glu Ser Gln Asp Glu Tyr Ala Tyr Arg Met
    50                  55                  60

Glu His Ile Met Ser Ser Trp Arg Glu Lys Val Asn Phe Pro Thr Val
65                  70                  75                  80

Tyr Ser Met Arg Leu Gln Leu Arg Arg Thr Ile Cys Lys Lys Phe Glu
                85                  90                  95

Glu Ser Leu Asp Ile Cys Pro Phe Gln Glu Ser His Gly Leu Asn Asn
            100                 105                 110

Thr Phe Thr Cys Leu Phe Thr Val Gly Thr Tyr Pro Trp Ile Thr Lys
        115                 120                 125

Phe Lys Leu Phe Arg Ser Val Cys Ser
```

-continued

```
<210> SEQ ID NO 19
<211> LENGTH: 18
<212> TYPE: DNA
<213> ORGANISM: Artificial Sequence
<220> FEATURE:
<223> OTHER INFORMATION: Oligonucleotide ZC20814

<400> SEQUENCE: 19
cacggtggag tttgtatc                                                 18

<210> SEQ ID NO 20
<211> LENGTH: 18
<212> TYPE: DNA
<213> ORGANISM: Artificial Sequence
<220> FEATURE:
<223> OTHER INFORMATION: Oligonucleotide ZC20815

<400> SEQUENCE: 20
gctgcacata gacatagg                                                 18

<210> SEQ ID NO 21
<211> LENGTH: 23
<212> TYPE: DNA
<213> ORGANISM: Artificial Sequence
<220> FEATURE:
<223> OTHER INFORMATION: Oligonucleotide ZC17516

<400> SEQUENCE: 21
aagtaagagt ggcaaggtgt ccc                                           23

<210> SEQ ID NO 22
<211> LENGTH: 22
<212> TYPE: DNA
<213> ORGANISM: Artificial Sequence
<220> FEATURE:
<223> OTHER INFORMATION: Oligonucleotide ZC17517

<400> SEQUENCE: 22
gcccgaacaa tgtgcaagaa ga                                            22
```